(12) United States Patent
Altshuler et al.

(10) Patent No.: US 8,328,796 B2
(45) Date of Patent: *Dec. 11, 2012

(54) LIGHT ENERGY DELIVERY HEAD

(75) Inventors: Gregory B. Altshuler, Lincoln, MA (US); Henry H. Zenzie, Dover, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,733

(22) Filed: Jul. 11, 2011

(65) Prior Publication Data

US 2011/0267830 A1 Nov. 3, 2011

Related U.S. Application Data

(60) Continuation of application No. 12/840,513, filed on Jul. 21, 2010, now Pat. No. 8,002,768, which is a division of application No. 11/301,340, filed on Dec. 12, 2005, now Pat. No. 7,763,016, which is a continuation of application No. 10/738,738, filed on Dec. 16, 2003, now Pat. No. 6,974,451, which is a continuation of application No. 10/052,474, filed on Jan. 18, 2002, now Pat. No. 6,663,620, which is a continuation of application No. 09/473,910, filed on Dec. 28, 1999, now Pat. No. 6,517,532, which is a continuation-in-part of application No. 09/078,055, filed on May 13, 1998, now Pat. No. 6,273,884.

(60) Provisional application No. 60/046,542, filed on May 15, 1997, provisional application No. 60/077,726, filed on Mar. 12, 1998, provisional application No. 60/115,447, filed on Jan. 8, 1999, provisional application No. 60/164,492, filed on Nov. 9, 1999.

(51) Int. Cl.
*A61B 18/18* (2006.01)
(52) U.S. Cl. ............................. 606/9; 606/13; 607/88
(58) Field of Classification Search .................. None
See application file for complete search history.

(56) References Cited

U.S. PATENT DOCUMENTS 853,033 A 5/1907 Roberts
(Continued)

FOREIGN PATENT DOCUMENTS

AT 400305 4/1995
(Continued)

OTHER PUBLICATIONS

Grossman, M.C. et al., "Damage to hair follicles by normal-mode ruby laser pulses," Journal of he American Academy of Dermatology, vol. 35, No. 6, pp. 889-894, Dec. 1996.
(Continued)

*Primary Examiner* — Gregory A Morse
*Assistant Examiner* — Lynsey Crandall
(74) *Attorney, Agent, or Firm* — Thomas J. Engellenner; Reza Mollaaghababa; Pepper Hamilton LLP

(57) ABSTRACT

A light energy delivery head is provided which, in one aspect, mounts laser diode bars or other light energy emitters in a heat sink block which is adapted to cool both the emitters and a surface of a medium with which the head is in contact and to which it is applying light energy. In another aspect, various retroreflection configurations are provided which optimize retroreflection of back-scattered light energy from the medium. The size of the aperture through which light energy is applied to the medium is also controlled so as to provide a desired amplification coefficient as a result of retroreflection.

16 Claims, 11 Drawing Sheets

U.S. PATENT DOCUMENTS

| | | |
|---|---|---|
| 1,590,283 A | 6/1926 | Catlin |
| 1,676,183 A | 7/1928 | Garfunkle |
| 1,706,161 A | 3/1929 | Hollnagen |
| 2,472,385 A | 6/1949 | Rollman |
| 2,669,771 A | 2/1954 | Burge et al. |
| 3,261,978 A | 7/1966 | Brenman |
| 3,327,712 A | 6/1967 | Kaufmann |
| 3,486,070 A | 12/1969 | Engel |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,653,778 A | 4/1972 | Freiling |
| 3,667,454 A | 6/1972 | Prince |
| 3,693,623 A | 9/1972 | Harte et al. |
| 3,793,723 A | 2/1974 | Kuris et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz et al. |
| 3,909,649 A | 9/1975 | Arsena |
| 3,939,560 A | 2/1976 | Lyall |
| 3,977,083 A | 8/1976 | Leslie et al. |
| 4,047,106 A | 9/1977 | Robinson |
| 4,213,462 A | 7/1980 | Sato |
| 4,233,493 A | 11/1980 | Nath et al. |
| 4,254,333 A | 3/1981 | Bergstrom |
| 4,269,067 A | 5/1981 | Tynan et al. |
| 4,273,109 A | 6/1981 | Enderby |
| 4,275,335 A | 6/1981 | Ishida |
| 4,298,005 A | 11/1981 | Mutzhas |
| 4,316,467 A | 2/1982 | Muckerheide |
| 4,333,197 A | 6/1982 | Kuris |
| 4,335,726 A | 6/1982 | Kolstedt |
| 4,388,924 A | 6/1983 | Weissman et al. |
| 4,409,479 A | 10/1983 | Sprague et al. |
| 4,452,081 A | 6/1984 | Seppi |
| 4,456,872 A | 6/1984 | Froeschle |
| 4,461,294 A | 7/1984 | Baron |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle |
| 4,561,440 A | 12/1985 | Kubo et al. |
| 4,566,271 A | 1/1986 | French et al. |
| 4,591,762 A | 5/1986 | Nakamura |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,653,495 A | 3/1987 | Nanaumi |
| 4,677,347 A | 6/1987 | Nakamura et al. |
| 4,686,986 A | 8/1987 | Fenyo et al. |
| 4,695,697 A | 9/1987 | Kosa |
| 4,710,677 A | 12/1987 | Halberstadt et al. |
| 4,718,416 A | 1/1988 | Nanaumi |
| 4,733,660 A | 3/1988 | Itzkan |
| 4,736,745 A | 4/1988 | Gluckman |
| 4,745,909 A | 5/1988 | Pelton et al. |
| 4,747,660 A | 5/1988 | Nishioka et al. |
| 4,749,913 A | 6/1988 | Stuermer et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,819,669 A | 4/1989 | Politzer |
| 4,826,431 A | 5/1989 | Fujimura et al. |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,852,549 A | 8/1989 | Mori et al. |
| 4,860,172 A | 8/1989 | Schlager et al. |
| 4,860,744 A | 8/1989 | Johnson et al. |
| 4,862,903 A | 9/1989 | Campbell |
| 4,871,479 A | 10/1989 | Bachelard et al. |
| 4,884,560 A | 12/1989 | Kuracina |
| 4,898,438 A | 2/1990 | Mori |
| 4,905,690 A | 3/1990 | Ohshiro et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,932,954 A | 6/1990 | Wondrazek et al. |
| 4,945,239 A | 7/1990 | Wist et al. |
| 4,973,848 A | 11/1990 | Kolobanov et al. |
| 4,976,308 A | 12/1990 | Faghri |
| 4,979,180 A | 12/1990 | Muncheryan |
| 4,992,256 A | 2/1991 | Skaggs et al. |
| 5,000,752 A | 3/1991 | Hoskin et al. |
| 5,030,090 A | 7/1991 | Maeda et al. |
| 5,032,178 A | 7/1991 | Cornell |
| 5,046,494 A | 9/1991 | Searfoss et al. |
| 5,050,597 A | 9/1991 | Daikuzono |
| 5,057,104 A | 10/1991 | Chess |
| 5,059,192 A | 10/1991 | Zaias |
| 5,065,515 A | 11/1991 | Iderosa |
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,133,102 A | 7/1992 | Sakuma et al. |
| 5,137,530 A | 8/1992 | Sand |
| 5,140,984 A | 8/1992 | Dew et al. |
| 5,159,601 A | 10/1992 | Huber |
| 5,160,194 A | 11/1992 | Feldman |
| 5,171,564 A | 12/1992 | Nathoo et al. |
| 5,178,617 A | 1/1993 | Kuizenga et al. |
| 5,182,557 A | 1/1993 | Lang |
| 5,182,857 A | 2/1993 | Simon |
| 5,192,278 A | 3/1993 | Hayes et al. |
| 5,196,004 A | 3/1993 | Sinofsky |
| 5,207,671 A | 5/1993 | Franken et al. |
| 5,222,907 A | 6/1993 | Katabuchi et al. |
| 5,225,926 A | 7/1993 | Cuomo et al. |
| 5,226,907 A | 7/1993 | Tankovich |
| 5,267,399 A | 12/1993 | Johnston |
| 5,281,211 A | 1/1994 | Parel et al. |
| 5,282,797 A | 2/1994 | Chess |
| 5,287,372 A | 2/1994 | Ortiz |
| 5,287,380 A | 2/1994 | Hsia |
| 5,293,880 A | 3/1994 | Levitt |
| 5,300,097 A | 4/1994 | Lerner et al. |
| 5,303,585 A | 4/1994 | Lichte |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,336,217 A | 8/1994 | Buys et al. |
| 5,342,358 A | 8/1994 | Daikuzono et al. |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,353,020 A | 10/1994 | Schurmann |
| 5,353,790 A | 10/1994 | Jacques et al. |
| 5,356,081 A | 10/1994 | Sellar |
| 5,358,503 A | 10/1994 | Bertwell et al. |
| 5,360,426 A | 11/1994 | Muller et al. |
| 5,369,831 A | 12/1994 | Bock |
| 5,380,317 A | 1/1995 | Everett et al. |
| 5,386,427 A | 1/1995 | Zayhowski |
| 5,403,306 A | 4/1995 | Edwards et al. |
| 5,405,368 A | 4/1995 | Eckhouse |
| 5,409,446 A | 4/1995 | Rattner |
| 5,415,654 A | 5/1995 | Daikuzono |
| 5,422,112 A | 6/1995 | Williams |
| 5,425,728 A | 6/1995 | Tankovich |

| | | | | | |
|---|---|---|---|---|---|
| 5,425,735 A | 6/1995 | Rosen et al. | 5,820,626 A | 10/1998 | Baumgardner |
| 5,425,754 A | 6/1995 | Braun et al. | 5,824,023 A | 10/1998 | Anderson |
| 5,445,608 A | 8/1995 | Chen et al. | 5,827,264 A | 10/1998 | Hohla |
| 5,445,611 A | 8/1995 | Eppstein et al. | 5,828,803 A | 10/1998 | Eckhouse |
| 5,454,807 A | 10/1995 | Lennox et al. | 5,830,208 A | 11/1998 | Muller |
| 5,458,140 A | 10/1995 | Eppstein et al. | 5,835,648 A | 11/1998 | Narciso, Jr. et al. |
| 5,474,549 A | 12/1995 | Ortiz et al. | 5,836,877 A | 11/1998 | Zavislan |
| 5,486,170 A | 1/1996 | Winston et al. | 5,836,999 A | 11/1998 | Eckhouse et al. |
| 5,486,172 A | 1/1996 | Chess | 5,840,048 A | 11/1998 | Cheng |
| 5,501,680 A | 3/1996 | Kurtz et al. | 5,849,029 A | 12/1998 | Eckhouse et al. |
| 5,502,582 A | 3/1996 | Larson et al. | 5,851,181 A | 12/1998 | Talmor |
| 5,505,726 A | 4/1996 | Meserol | 5,853,407 A | 12/1998 | Miller |
| 5,505,727 A | 4/1996 | Keller | 5,860,967 A | 1/1999 | Zavislan et al. |
| 5,519,534 A | 5/1996 | Smith et al. | 5,868,731 A | 2/1999 | Budnik et al. |
| 5,522,813 A | 6/1996 | Trelles | 5,868,732 A | 2/1999 | Waldman et al. |
| 5,527,368 A | 6/1996 | Supkis et al. | 5,871,480 A | 2/1999 | Tankovich |
| 5,531,739 A | 7/1996 | Trelles | 5,879,159 A | 3/1999 | Cipolla |
| 5,531,740 A | 7/1996 | Black | 5,883,471 A | 3/1999 | Rodman et al. |
| 5,536,168 A | 7/1996 | Bourke et al. | 5,885,211 A | 3/1999 | Eppstein et al. |
| 5,549,660 A | 8/1996 | Mendes et al. | 5,885,273 A | 3/1999 | Eckhouse et al. |
| 5,558,667 A | 9/1996 | Yarborough et al. | 5,885,274 A | 3/1999 | Fullmer et al. |
| 5,561,881 A | 10/1996 | Klinger et al. | 5,891,063 A | 4/1999 | Vigil |
| 5,571,098 A | 11/1996 | Domankevitz et al. | 5,893,828 A | 4/1999 | Uram |
| 5,578,866 A | 11/1996 | DePoorter et al. | 5,895,350 A | 4/1999 | Hori |
| 5,595,568 A | 1/1997 | Anderson et al. | 5,897,549 A | 4/1999 | Tankovich |
| 5,611,793 A | 3/1997 | Wilson et al. | 5,906,609 A | 5/1999 | Assa et al. |
| 5,616,140 A | 4/1997 | Prescott | 5,908,418 A | 6/1999 | Dority et al. |
| 5,618,284 A | 4/1997 | Sand | 5,913,883 A | 6/1999 | Alexander et al. |
| 5,620,478 A | 4/1997 | Eckhouse et al. | 5,916,211 A | 6/1999 | Quon et al. |
| 5,626,631 A | 5/1997 | Eckhouse et al. | 5,920,374 A | 7/1999 | Vaphiades et al. |
| 5,628,744 A | 5/1997 | Coleman et al. | 5,921,926 A | 7/1999 | Rolland et al. |
| 5,630,811 A | 5/1997 | Miller | 5,928,222 A | 7/1999 | Kleinerman |
| 5,634,711 A | 6/1997 | Kennedy et al. | 5,944,687 A | 8/1999 | Benett et al. |
| 5,649,972 A | 7/1997 | Hochstein | 5,944,748 A | 8/1999 | Mager et al. |
| 5,652,481 A | 7/1997 | Johnson et al. | 5,948,011 A | 9/1999 | Knowlton |
| 5,653,706 A | 8/1997 | Zavislan et al. | 5,949,222 A | 9/1999 | Buono |
| 5,655,547 A | 8/1997 | Karni | 5,954,710 A | 9/1999 | Paolini et al. |
| 5,657,760 A | 8/1997 | Ying et al. | 5,955,490 A | 9/1999 | Kennedy et al. |
| 5,658,148 A | 8/1997 | Neuberger et al. | 5,957,915 A | 9/1999 | Trost |
| 5,658,323 A | 8/1997 | Miller | 5,964,749 A | 10/1999 | Eckhouse et al. |
| 5,660,836 A | 8/1997 | Knowlton | 5,968,033 A | 10/1999 | Fuller et al. |
| 5,661,744 A | 8/1997 | Murakami et al. | 5,968,034 A | 10/1999 | Fullmer et al. |
| 5,662,643 A | 9/1997 | Kung et al. | 5,974,059 A | 10/1999 | Dawson |
| 5,662,644 A | 9/1997 | Swor | 5,974,616 A | 11/1999 | Dreyfus |
| 5,673,451 A | 10/1997 | Moore et al. | 5,977,723 A | 11/1999 | Yoon |
| 5,679,113 A | 10/1997 | Caisey et al. | 5,979,454 A | 11/1999 | Anvari et al. |
| 5,683,380 A | 11/1997 | Eckhouse et al. | 5,984,915 A | 11/1999 | Loeb et al. |
| 5,692,509 A | 12/1997 | Voss et al. | 6,007,219 A | 12/1999 | O'Meara |
| 5,698,866 A | 12/1997 | Doiron et al. | 6,015,404 A | 1/2000 | Altshuler et al. |
| 5,707,403 A | 1/1998 | Grove et al. | 6,022,316 A | 2/2000 | Eppstein et al. |
| 5,707,409 A | 1/1998 | Martin et al. | 6,026,828 A | 2/2000 | Altshuler |
| 5,713,738 A | 2/1998 | Yarborough | 6,027,495 A | 2/2000 | Miller |
| 5,714,119 A | 2/1998 | Kawagoe et al. | 6,029,303 A | 2/2000 | Dewan |
| 5,720,772 A | 2/1998 | Eckhouse | 6,029,304 A | 2/2000 | Hulke et al. |
| 5,722,397 A | 3/1998 | Eppstein | 6,030,378 A | 2/2000 | Stewart |
| 5,725,522 A | 3/1998 | Sinofsky | 6,030,399 A | 2/2000 | Ignotz et al. |
| 5,728,090 A | 3/1998 | Martin et al. | 6,032,071 A | 2/2000 | Binder |
| 5,735,844 A | 4/1998 | Anderson et al. | RE36,634 E | 3/2000 | Ghaffari |
| 5,735,884 A | 4/1998 | Thompson et al. | 6,036,684 A | 3/2000 | Tankovich et al. |
| 5,738,678 A | 4/1998 | Patel | 6,044,514 A | 4/2000 | Kaneda et al. |
| 5,742,392 A | 4/1998 | Anderson et al. | 6,050,990 A | 4/2000 | Tankovich et al. |
| 5,743,901 A | 4/1998 | Grove et al. | D424,197 S | 5/2000 | Sydlowski et al. |
| 5,743,902 A | 4/1998 | Trost | 6,056,548 A | 5/2000 | Neuberger et al. |
| 5,746,735 A | 5/1998 | Furumoto et al. | 6,056,738 A | 5/2000 | Marchitto et al. |
| 5,748,822 A | 5/1998 | Miura et al. | 6,058,937 A | 5/2000 | Doiron et al. |
| 5,755,751 A | 5/1998 | Eckhouse | 6,059,820 A | 5/2000 | Baronov |
| 5,759,200 A | 6/1998 | Azar | 6,063,108 A | 5/2000 | Salansky et al. |
| 5,760,362 A | 6/1998 | Eloy | 6,070,092 A | 5/2000 | Kazama et al. |
| 5,769,076 A | 6/1998 | Maekawa et al. | 6,071,239 A | 6/2000 | Cribbs et al. |
| 5,782,249 A | 7/1998 | Weber et al. | 6,074,382 A | 6/2000 | Asah et al. |
| 5,802,136 A | 9/1998 | Carol | 6,080,146 A | 6/2000 | Altshuler et al. |
| 5,810,801 A | 9/1998 | Anderson et al. | 6,080,147 A | 6/2000 | Tobinick |
| 5,812,567 A | 9/1998 | Jeon et al. | 6,083,217 A | 7/2000 | Tankovich |
| 5,813,855 A | 9/1998 | Crisio, Jr. | 6,086,363 A | 7/2000 | Moran et al. |
| 5,814,008 A | 9/1998 | Chen et al. | 6,086,580 A | 7/2000 | Mordon et al. |
| 5,814,040 A | 9/1998 | Nelson et al. | 6,094,767 A | 8/2000 | Iimura |
| 5,814,041 A | 9/1998 | Anderson et al. | 6,096,029 A | 8/2000 | O'Donnell, Jr. |
| 5,817,089 A | 10/1998 | Tankovich et al. | 6,096,209 A | 8/2000 | O'Brien et al. |
| 5,820,625 A | 10/1998 | Izawa et al. | 6,099,521 A | 8/2000 | Shadduck |

| | | |
|---|---|---|
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,171,300 B1 | 1/2001 | Adams |
| 6,171,301 B1 | 1/2001 | Nelson |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,075 B1 | 5/2001 | Furumoto |
| 6,229,831 B1 | 5/2001 | Nightingale et al. |
| 6,235,015 B1 | 5/2001 | Mead, III et al. |
| 6,235,016 B1 | 5/2001 | Stewart |
| 6,236,891 B1 | 5/2001 | Ingle et al. |
| 6,239,442 B1 | 5/2001 | Iimura et al. |
| 6,240,306 B1 | 5/2001 | Rohrscheib et al. |
| 6,245,093 B1 | 6/2001 | Li et al. |
| 6,251,127 B1 | 6/2001 | Biel |
| 6,254,388 B1 | 7/2001 | Yarborough |
| 6,263,233 B1 | 7/2001 | Zavislan et al. |
| 6,264,649 B1 * | 7/2001 | Whitcroft et al. ............... 606/22 |
| 6,267,779 B1 | 7/2001 | Gerdes |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,325,769 B1 | 12/2001 | Klopotek |
| 6,328,733 B1 | 12/2001 | Trost |
| 6,331,111 B1 | 12/2001 | Cao |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,395,016 B1 | 5/2002 | Oron et al. |
| 6,400,011 B1 | 6/2002 | Miki |
| 6,402,739 B1 | 6/2002 | Neev |
| 6,406,474 B1 | 6/2002 | Neuberger et al. |
| 6,409,665 B1 | 6/2002 | Scott et al. |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,978 B1 | 9/2002 | Zharov |
| 6,451,007 B1 | 9/2002 | Koop et al. |
| 6,461,296 B1 | 10/2002 | Desai |
| 6,464,694 B1 | 10/2002 | Massengill |
| 6,471,712 B2 | 10/2002 | Burres |
| 6,471,716 B1 | 10/2002 | Pecukonis |
| 6,475,211 B2 | 11/2002 | Chess et al. |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,494,900 B1 | 12/2002 | Salansky et al. |
| 6,497,702 B1 | 12/2002 | Bernaz |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,616,447 B1 | 9/2003 | Rizoiu |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,675,425 B1 | 1/2004 | Iimura et al. |
| 6,676,654 B1 | 1/2004 | Balle-Petersen et al. |
| 6,679,837 B2 | 1/2004 | Daikuzono |

| Patent | Date | Inventor(s) |
|---|---|---|
| 6,685,639 B1 | 2/2004 | Wang et al. |
| 6,685,699 B1 | 2/2004 | Eppstein et al. |
| 6,689,124 B1 | 2/2004 | Thiberg |
| 6,692,456 B1 | 2/2004 | Eppstein et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,746,444 B2 | 6/2004 | Key |
| 6,749,623 B1 | 6/2004 | Hsi et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| RE38,670 E | 12/2004 | Asah et al. |
| 6,858,009 B2 | 2/2005 | Kawata et al. |
| 6,860,879 B2 | 3/2005 | Irion et al. |
| 6,862,771 B1 | 3/2005 | Muller |
| 6,863,781 B2 | 3/2005 | Nocera et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,936,046 B2 | 8/2005 | Hissong et al. |
| 6,942,658 B1 | 9/2005 | Rizoiu et al. |
| 6,953,341 B2 | 10/2005 | Black |
| 6,974,451 B2 | 12/2005 | Altshuler et al. |
| 6,976,985 B2 | 12/2005 | Altshuler et al. |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,029,469 B2 | 4/2006 | Vasily |
| 7,033,349 B2 | 4/2006 | Key |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,182,760 B2 | 2/2007 | Kubota |
| 7,198,634 B2 | 4/2007 | Harth et al. |
| 7,204,832 B2 | 4/2007 | Altshuler et al. |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,351,252 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler et al. |
| 7,531,967 B2 | 5/2009 | Inochkin et al. |
| 7,540,869 B2 | 6/2009 | Altshuler et al. |
| 7,624,640 B2 | 12/2009 | Maris et al. |
| 7,647,092 B2 | 1/2010 | Motz et al. |
| 7,758,621 B2 | 7/2010 | Altshuler et al. |
| 7,763,016 B2 | 7/2010 | Altshuler et al. |
| 7,935,107 B2 | 5/2011 | Altshuler et al. |
| 7,938,821 B2 | 5/2011 | Chan et al. |
| 7,942,915 B2 | 5/2011 | Altshuler et al. |
| 7,942,916 B2 | 5/2011 | Altshuler et al. |
| 8,002,768 B1 | 8/2011 | Altshuler et al. |
| 2001/0007068 A1 | 7/2001 | Ota et al. |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0026225 A1 | 2/2002 | Segal |
| 2002/0029071 A1 | 3/2002 | Whitehurst |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0161357 A1 | 10/2002 | Anderson et al. |
| 2002/0161418 A1 | 10/2002 | Wilkens et al. |
| 2002/0173780 A1 | 11/2002 | Altshuler et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0083649 A1 | 5/2003 | Margaron et al. |
| 2003/0084534 A1 | 5/2003 | Kaizuka |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0163884 A1 | 9/2003 | Weihrauch |
| 2003/0167080 A1 | 9/2003 | Hart et al. |
| 2003/0169433 A1 | 9/2003 | Koele et al. |

| | | |
|---|---|---|
| 2003/0181896 A1 | 9/2003 | Zvuloni et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | Debenedictis et al. |
| 2003/0216795 A1 | 11/2003 | Harth et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0111132 A1 | 6/2004 | Shenderova et al. |
| 2004/0116984 A1 | 6/2004 | Spooner et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162549 A1 | 8/2004 | Altshuler |
| 2004/0162596 A1 | 8/2004 | Altshuler et al. |
| 2004/0176754 A1 | 9/2004 | Island et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065531 A1 | 3/2005 | Cohen |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0143719 A1 | 6/2005 | Sink |
| 2005/0168158 A1 | 8/2005 | Inochkin et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0182389 A1 | 8/2005 | LaPorte et al. |
| 2005/0197681 A1 | 9/2005 | Barolet et al. |
| 2005/0215988 A1 | 9/2005 | Altshuler et al. |
| 2005/0220726 A1 | 10/2005 | Pauly et al. |
| 2005/0251118 A1 | 11/2005 | Anderson et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0047281 A1 | 3/2006 | Kreindel |
| 2006/0058712 A1 | 3/2006 | Altshuler et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0122668 A1 | 6/2006 | Anderson et al. |
| 2006/0149343 A1 | 7/2006 | Altshulter et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 2/2007 | Altshuler et al. |
| 2007/0049910 A1 | 3/2007 | Altshuler et al. |
| 2007/0060819 A1 | 3/2007 | Altshuler et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0121069 A1 | 5/2007 | Andersen et al. |
| 2007/0159592 A1 | 7/2007 | Rylander et al. |
| 2007/0185552 A1 | 8/2007 | Masotti et al. |
| 2007/0194717 A1 | 8/2007 | Belikov et al. |
| 2007/0198004 A1 | 8/2007 | Altshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0255355 A1 | 11/2007 | Altshuler et al. |
| 2007/0288071 A1 | 12/2007 | Rogers |
| 2008/0009842 A1 | 1/2008 | Manstein et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0195183 A1 | 8/2008 | Botchkareva et al. |
| 2008/0214988 A1 | 9/2008 | Altshuler et al. |
| 2008/0294150 A1 | 11/2008 | Altshuler et al. |
| 2008/0294152 A1 | 11/2008 | Altshuler et al. |
| 2008/0306471 A1 | 12/2008 | Altshuler et al. |
| 2008/0319430 A1 | 12/2008 | Zenzie et al. |
| 2009/0048557 A1 | 2/2009 | Yeshurun et al. |
| 2009/0069741 A1 | 3/2009 | Altshuler et al. |
| 2009/0137995 A1 | 5/2009 | Altshuler et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2010/0036295 A1 | 2/2010 | Altshuler et al. |
| 2010/0145321 A1 | 6/2010 | Altshuler et al. |
| 2010/0204686 A1 | 8/2010 | Yaroslavksy et al. |
| 2010/0286673 A1 | 11/2010 | Altshuler et al. |
| 2010/0298744 A1 | 11/2010 | Altshuler et al. |
| 2011/0046523 A1 | 2/2011 | Altshuler et al. |
| 2011/0137230 A1 | 6/2011 | Altshuler et al. |
| 2011/0172651 A1 | 7/2011 | Altshuler et al. |
| 2011/0184334 A1 | 7/2011 | Altshuler et al. |
| 2011/0267830 A1 | 11/2011 | Altshuler et al. |

FOREIGN PATENT DOCUMENTS

| | | |
|---|---|---|
| AU | 1851583 A | 3/1984 |
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| DE | 3304230 A1 | 8/1984 |
| DE | 3719561 A1 | 1/1988 |
| DE | 3837248 A1 | 5/1990 |
| DE | 9102407 U1 | 7/1991 |
| DE | 19803460 C1 | 8/1999 |
| DE | 19944401 A1 | 3/2001 |
| DE | 10140715 A1 | 3/2002 |
| DE | 10112289 A1 | 9/2002 |
| DE | 10120787 A1 | 1/2003 |
| EP | 0000593 A1 | 2/1979 |
| EP | 0142671 A1 | 5/1985 |
| EP | 0172490 A1 | 2/1986 |

| | | | | | | |
|---|---|---|---|---|---|---|
| EP | 0320080 A1 | 6/1989 | | JP | 2009106767 A | 4/2009 |
| EP | 0324120 A1 | 7/1989 | | JP | 2009136691 A | 6/2009 |
| EP | 0563953 A2 | 10/1993 | | RU | 2082337 C1 | 6/1997 |
| EP | 0565331 A2 | 10/1993 | | RU | 2089126 C1 | 9/1997 |
| EP | 0593375 A1 | 4/1994 | | RU | 2089127 C1 | 9/1997 |
| EP | 0598984 | 6/1994 | | RU | 2096051 C1 | 11/1997 |
| EP | 0709941 A1 | 5/1996 | | RU | 2122848 C1 | 12/1998 |
| EP | 0724894 A2 | 8/1996 | | WO | 86/02783 | 5/1986 |
| EP | 0726083 A2 | 8/1996 | | WO | 88/04592 | 6/1988 |
| EP | 0736308 A2 | 10/1996 | | WO | 90/00420 | 1/1990 |
| EP | 0743029 A2 | 11/1996 | | WO | 91/02562 | 3/1991 |
| EP | 0755698 A2 | 1/1997 | | WO | 91/13652 | 9/1991 |
| EP | 0763371 A2 | 3/1997 | | WO | 92/16338 | 1/1992 |
| EP | 0765673 A2 | 4/1997 | | WO | 92/19165 | 11/1992 |
| EP | 0765674 A2 | 4/1997 | | WO | 93/05920 | 4/1993 |
| EP | 0783904 A2 | 7/1997 | | WO | 95/10243 | 4/1995 |
| EP | 0884066 A2 | 12/1998 | | WO | 95/15725 | 6/1995 |
| EP | 0885629 A2 | 12/1998 | | WO | 95/32441 | 11/1995 |
| EP | 0920840 A2 | 6/1999 | | WO | 96/22741 | 8/1996 |
| EP | 0 927 544 A2 | 7/1999 | | WO | 96/23447 | 8/1996 |
| EP | 1038505 A2 | 9/2000 | | WO | 96/24406 A1 | 8/1996 |
| EP | 1057454 A2 | 12/2000 | | WO | 96/25979 | 8/1996 |
| EP | 1075854 A2 | 2/2001 | | WO | 9628212 A1 | 9/1996 |
| EP | 1138349 A2 | 10/2001 | | WO | 9636396 | 11/1996 |
| EP | 1147785 A2 | 10/2001 | | WO | 9641579 | 12/1996 |
| EP | 1219258 A1 | 7/2002 | | WO | 97/13458 | 4/1997 |
| EP | 1226787 A2 | 7/2002 | | WO | 97/13552 | 4/1997 |
| EP | 1 238 683 A1 | 9/2002 | | WO | 97/22384 | 6/1997 |
| EP | 1250893 | 10/2002 | | WO | 97/28752 A1 | 8/1997 |
| EP | 1457234 | 9/2004 | | WO | 98/04317 | 2/1998 |
| EP | 1495735 A1 | 1/2005 | | WO | 98/05286 | 2/1998 |
| EP | 1512373 A1 | 3/2005 | | WO | 98/05380 A1 | 2/1998 |
| EP | 1535582 A1 | 6/2005 | | WO | 98/06456 | 2/1998 |
| EP | 1627662 A1 | 2/2006 | | WO | 98/07379 | 2/1998 |
| EP | 1839705 A1 | 10/2007 | | WO | 98/20937 | 5/1998 |
| EP | 1854505 A2 | 11/2007 | | WO | 98/24507 | 6/1998 |
| FR | 2199453 A1 | 4/1974 | | WO | 98/29134 A2 | 7/1998 |
| FR | 2591902 A1 | 6/1987 | | WO | 98/41158 | 9/1998 |
| GB | 1546625 A | 5/1979 | | WO | 98/51235 | 11/1998 |
| GB | 2044908 A | 10/1980 | | WO | 98/52481 | 11/1998 |
| GB | 2059053 A | 4/1981 | | WO | 98/58595 | 12/1998 |
| GB | 2059054 A | 4/1981 | | WO | 99/10046 | 3/1999 |
| GB | 2123287 A | 2/1984 | | WO | 99/17668 A1 | 4/1999 |
| GB | 2239675 A | 7/1991 | | WO | 9917666 A1 | 4/1999 |
| GB | 2270159 A | 3/1994 | | WO | 9917667 | 4/1999 |
| GB | 2356570 A | 5/2001 | | WO | 99/27997 | 6/1999 |
| GB | 2360461 A | 9/2001 | | WO | 99/29243 | 6/1999 |
| GB | 2360946 A | 10/2001 | | WO | 99/34867 | 7/1999 |
| GB | 2364376 A | 1/2002 | | WO | 99/38569 | 8/1999 |
| GB | 2368020 A | 4/2002 | | WO | 99/43387 | 9/1999 |
| GB | 2390021 A | 12/2003 | | WO | 99/44638 | 9/1999 |
| GB | 2397528 A | 7/2004 | | WO | 99/46005 | 9/1999 |
| JP | 54129791 | 10/1979 | | WO | 99/49937 | 10/1999 |
| JP | 64-027554 A | 1/1989 | | WO | 99/62472 | 12/1999 |
| JP | 10-099574 A | 4/1989 | | WO | 99/66988 | 12/1999 |
| JP | 01-181877 A | 7/1989 | | WO | 0002491 | 1/2000 |
| JP | 02-013014 Y2 | 4/1990 | | WO | 0003257 A1 | 1/2000 |
| JP | 02-174804 A | 7/1990 | | WO | 0007514 | 2/2000 |
| JP | 03066387 A | 3/1991 | | WO | 00/30714 | 6/2000 |
| JP | 06-022871 A | 2/1994 | | WO | 0032272 A1 | 6/2000 |
| JP | 07-063957 A | 3/1995 | | WO | 00/41278 | 7/2000 |
| JP | 09-084803 A | 3/1997 | | WO | 0040266 A2 | 7/2000 |
| JP | 9141869 A | 6/1997 | | WO | 0043070 A1 | 7/2000 |
| JP | 10-014661 A | 1/1998 | | WO | 0044294 A1 | 8/2000 |
| JP | 10-503109 A | 3/1998 | | WO | 00/54685 | 9/2000 |
| JP | 10-165410 A | 6/1998 | | WO | 0054649 A2 | 9/2000 |
| JP | 11-047146 | 2/1999 | | WO | 00/62700 A1 | 10/2000 |
| JP | 2000-037400 | 2/2000 | | WO | 00/66226 | 11/2000 |
| JP | 2000-153003 A | 6/2000 | | WO | 0064537 | 11/2000 |
| JP | 2000-300684 | 10/2000 | | WO | 0071045 A1 | 11/2000 |
| JP | 2001-029124 A | 2/2001 | | WO | 0074583 A1 | 12/2000 |
| JP | 2001145520 A | 5/2001 | | WO | 0074781 A1 | 12/2000 |
| JP | 2001520534 A | 10/2001 | | WO | 0078242 A1 | 12/2000 |
| JP | 2001-343560 A | 12/2001 | | WO | 0103257 A1 | 1/2001 |
| JP | 2002506362 T | 2/2002 | | WO | 01/14012 A1 | 3/2001 |
| JP | 2002522110 A | 7/2002 | | WO | 0126573 A1 | 4/2001 |
| JP | 2002272861 A | 9/2002 | | WO | 0134048 A1 | 5/2001 |
| JP | 2005-017796 A | 1/2005 | | WO | 01/41872 A1 | 6/2001 |
| JP | 2005027702 A | 2/2005 | | WO | 0142671 A1 | 6/2001 |

| | | |
|---|---|---|
| WO | 0154606 A1 | 8/2001 |
| WO | 0154770 A1 | 8/2001 |
| WO | 0178830 A2 | 10/2001 |
| WO | 02/09813 | 2/2002 |
| WO | 0226147 | 4/2002 |
| WO | 02053050 A1 | 7/2002 |
| WO | 02069825 A2 | 9/2002 |
| WO | 02078559 | 10/2002 |
| WO | 02094116 A1 | 11/2002 |
| WO | 03/005883 | 1/2003 |
| WO | 03049633 | 6/2003 |
| WO | 2004/000150 | 12/2003 |
| WO | 2004/011848 | 2/2004 |
| WO | 2004/033040 | 4/2004 |
| WO | 2004/037068 A2 | 5/2004 |
| WO | 2004/037287 A2 | 5/2004 |
| WO | 2004/080279 | 9/2004 |
| WO | 2004073537 A2 | 9/2004 |
| WO | 2004084752 A2 | 10/2004 |
| WO | 2004086947 A2 | 10/2004 |
| WO | 2005007003 A1 | 1/2005 |
| WO | 2005009266 A1 | 2/2005 |
| WO | 2005/030317 | 4/2005 |
| WO | 2005/046793 | 5/2005 |
| WO | 2005/065288 | 7/2005 |
| WO | 2005/092438 | 10/2005 |
| WO | 2005/096981 | 10/2005 |
| WO | 2005/099369 | 10/2005 |
| WO | 2005112815 A1 | 12/2005 |
| WO | 2006/006123 | 1/2006 |
| WO | 2006036968 A2 | 4/2006 |
| WO | 2006/066226 | 6/2006 |
| WO | 2006/089227 | 8/2006 |
| WO | 2006/101735 A1 | 9/2006 |
| WO | 2006/116141 A1 | 11/2006 |
| WO | 2007/035444 | 3/2007 |
| WO | 2007/122611 | 11/2007 |
| WO | 2008/070747 | 6/2008 |

OTHER PUBLICATIONS

Grossman, M.C. et al., "Laser Targeted at Hair Follicles," Lasers Med Surg., Suppl. 7:221 (1995).
Hicks et al., "After Low Fluence Argon Laser and Flouride Treatment," Compendium, vol. 18, No. 6, Jun. 1997.
Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.
Hsu et al., "Combined Effects of Laser Irradiation/Solution Flouride Ion on Enamel Demineralization," Journal of Clinical Laser Medicine and Surgery, vol. 16, No. 2 pp. 93-105, 1998.
Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).
Hulsbergen Henning et al., "Port Wine Stain Coagulation Experiments with a 540-nm Continuous Wave Dye-Laser," Lasers in Surgery and Medicine, 2:205-210 (1983).
Invention description to certificate of authorship, No. 719439, "The ring resonator of optical quantum generator".
Invention description to certificate of authorship, No. 741747, "The modulator of optical radiation intensity".
Invention description to certificate of authorship, No. SU 1257475 A1, "Laser interferometric device to determine no-linearity of an index of refraction of optical medium".
Invention description to certificate of authorship, No. SU 1326962 A1, "The way of determination of non-linearity of an index of refraction of optical medium".
Invention description to certificate of autorship, No. 532304, "The way of investigation of radiation time structure of optical quantum generator".
[No Author] IPG Data Sheet for TFL Thulium Laser, Jun. 2001.
Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).
Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.
Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.
Karu, "Photobiological Fundamentals of Low-Power Laser Therapy," 8th Congress of International Society for Laser Surgery and Medicine, Mar. 30, 1987.
Kazmina et al., "Laser Prophlaxis and Treatment of Primary caries," SPIE vol. 1984, pp. 231-233.
Klein, E. et al., "Biological effects of laser radiation 1.,"Northeast Electroncis Research and Engineering Meeting, NEREM Record, IEEE catalogue No. F-60, pp. 108-109, 1965.
Kozlov et al., "Laser in Diagnostics and Treatment of Microcirculation Disorders Under Parodontitis," SPIE vol. 1984, pp. 253-264.
Kuhns, J.G. et al., "Biological effects of laser radiation II Effects of laser irradiation on the skin," NEREM Record, pp. 152-153, 1965.
Kuhns, J.G. et al., "Laser injury in skin," Laboratory Investigation, vol. 17, No. 1, pp. 1-13, Jul. 1967.
Levin, G. et al., "Designing with hyseretic current-mode control, " EDN Magazine, pp. 1-8, Apr. 11, 1996.
Levin, G. et al., "Designing with hyseretic current-mode control, " EDN Magazine, pp. 1-8, Apr. 28, 1994.
Maegawa, et al., "Effects of Near-Infrared Low-Level Laser Irradiation on Microcirculation," Lasers in Surgery and Medicine, vol. 27, pp. 427-437, 2000.
Mamedova et al., "Microbiological Estimate of Parodontis Laser Therapy Efficiency," SPIE vol. 1984, pp. 247-249.
Mang, "Effect of Soft Laser Treatment on Wound Healing in the Hamster Oral Mucosa," American Society for Laser Medicine and Surgery Abstracts, Chapters 25, pp. 5-8.
Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.
Margolis, R.J. et al., "Visible action spectrum for melanin-specific selective photothermolysis," Lasers in Surgery and Medicine, vol. 9, pp. 389-397, 1989.
Marinelli et al., "Diode laser illuminated automotive lamp systems," SPIE Proceedings vol. 3285:170-177 (1998).
Marshak, I.S., et al., "Pulsed Light Sources," State Power Engineering Press, Moscow and Leningrad (1963).
McDaniel, et al., "Hexascan: A New Robotized Scanning Laser Handpiece," Cutis, 45:300-305 (1990).
Nemeth, et al., "Copper vapor laser treatment of pigmented lesions," Lasers Surg. Med. Supp. 2:51 (1990).
Ohbayashi, "Stimulatory Effect of Laser Irradiation on Calcified Nodule Formation in Human Dental Pulp Fibroblasts," Abstract J-Endod. Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).
Ozawa et al., "Stimulatory Effects of Low-Power Laser Irradiation on Bone Formation in vitro," SPIE vol. 1984, pp. 281-288.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polla, L. et al., "Melanosomes are a primary target of Q-switched ruby laser irradiation in guinea pig skin," Journal of Investigative Dermatology, vol. 89, No. 3, pp. 281-286, Sep. 1987.

Powell, "Laser Dental Decay Prevention: does it have a future?" SPIE vol. 3192, 1997.

Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).

Remillard et al., "Diode Laser Illuminators for Night-Vision Applications," SPIE Proceedings vol. 4285:14-22 (2001).

Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).

Rohrer, "Evaluating the Safety and Efficacy of a Novel Light Based Hair Removal System," Lasers. Surg. Med. Supp.13:97 (2001).

Rotteleur, et al., "Robotized scanning laser handpiece for the treatment of port wine stains and other angiodysplasias," Lasers Surg. Med., 8:283-287 (1998).

Rubach et al., "Histological and Clinical Evaluation of Facial Resurfacing Using a Carbon Dioxide Laser With the Computer Pattern Generator," Arch Otolaryngol Head Neck Surg., 123:929-934 (1997).

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).

Sandford et al., "Thermal Effects During Desensitisation of Teeth with Gallium-Aluminum-Arsenide Lasers," University of Queensland Dental School, Periodontology 15: 25-30 (1994).

Schindl, "Does Low Intensity Laser Irradiation Really Cause Cell Damage?" Laser in Surgery and Medicine vol. 22, pp. 105, 2001.

Sheehan-Dare, et al., "Lasers in Dermatology," British Journal of Dermatology, 129:1-8 (1993).

Shimbashi, T. et al., "Ruby laser treatment of pigmented skin lesions," Aesth. Plast. Surg., vol. 19, pp. 225-229, 1995.

Shimizu et al., "Prospect of Relieving Pain Due to Tooth Movement During Orthodontic Treatment Utilizing a Ga-Al As Diode Laser," SPIE vol. 1984, pp. 275-280.

Shumilovitch et al., "Influence of Low Intensity Laser Radiation Upon the Microflora of Carious Cavities and Root Canal," SPIE vol. 1984, pp. 215-220.

Sing, "Electroacupuncture and Laser Stimulation Treatment: Evaluation by Somatosensory Evoked Potential in Conscious Rabbits," Abstract AM-J-Chin-Med. 1997; 25(3-4): 263-71.

Sliney et al., "Safety with Lasers and Other Optical Sources: A Comprehensive Handbook," Plenum Press, pp. 477-480 (1980).

Sokolova et al., "Low-intense Laser Radiation in Complex Treatment of Inflammatory Diseases of Parodontium," SPIE vol. 1984, pp. 234-237.

Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Sumian, C.C. et al., "A Preliminary Clinical and Histopathological Study of Laser Skin Resurfacing Using a frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using A Frequency Doubled Nd:YAG Laser After Topical Application of an Exogenous Chromophore," Lasers in Surgery and Medicine, vol. 25, pp. 43-50, 1999.

Taylor, C.R. et al., "Treatment of tattoos by Q-switched ruby laser," Arch. Dermatol. vol. 126, pp. 893-899, Jul. 1990.

Togatov, V.V. et al., "Discharge Circuit for Solid-State Lasers Pumping," Optical Journal, V. 67, n. 4, pp. 92-96 (2000).

Tuchin, V.V., "Laser light scattering in biomedical diagnostics and therapy," Journal of Laser Applications, vol. 5, No. 2-3, pp. 43-60, 1993.

Unger, W.P., Laser hair transplantation III: Computer-assisted laser transplanting. Dermatol Surg. 1995;21:1047-1055

Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992.

Walsh, "Laser "Curettage": a Critical Analysis," Periodontology 14:4-12, 1993.

Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.

Watanabe, S. S et al., "Comparative studies of femtosecond to microsecond laser pulses on selective pigmented cell injury in skin," Photochemistry and Photobiology, vol. 53, No. 6, pp. 757-762, 1991.

Watanabe, S. et al., "The Effect of Pulse Duration on Selective Pigmented Cell Injury by Dye Lasers," The Journal of Investigative Dermatology, 88:523, 1987.

Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.

Yules, R.B. et al., "The Effect of Q-switched ruby laser radiation on dermal tattoo pigment in man," Arch Surg, vol. 95, pp. 179-180, Aug. 1967.

Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.

Zonios et al., "Skin Melanin, Hemoglobin, and Light Scattering Properties can be Quantitatively Assessed in Vivo Using Diffuse Reflectance Spectroscopy," Journal of Investigative Dermatology,117:1452-1457 (Dec. 2001).

[No Author] BIOPTRON Light Therapy System. Website print-out, accessed Jul. 13, 2006 (2 pages).

[No Author] Derma Chiller advertisement (2 pages) from Paradigm Trex.

[No Author] Webpage www.gallery.com—RUTILE (Titanium Oxide)—Retrieved Oct. 3, 2011 from Http://www.galleries.com/minerals/oxides/rutile/rutile.htm. 2 pages.

Altea Therapeutics—Medicines Made Better (single page website print-out).

Altshuler et al., "Human Tooth as an Optical Device," SPIE vol. 1429 Holography and Interferometry and Optical Pattern Recognition in Biomedicine, pp. 95-104, 1991.

Altshuler et al., "Modern Optics and Dentistry," Laser in Dentistry, pp. 283-297, 1995.

Altshuler et al., "New Optical Effects in the Human Hard Tooth Tissues," Lasers and Medicine, Proc. SPIE vol. 1353, pp. 97-102, 1989.

Altshuler, G.B. et al., "Acoustic response of hard dental tissues to pulsed laser action," SPIE, vol. 2080, Dental Application of Lasers, pp. 97-103, 1993.

Altshuler, G.B. et al., "Extended theory of selective photothermolysis," Lasers in Surgery and Medicine, vol. 29, pp. 416-432, 2001.

Amy, R.L. et al., "Selective mitochondrial damage by a ruby laser microbeam: An electron microscopic study," Science, vol. 15, pp. 756-758, Nov. 1965.

Anderson, R.R. et al., "Selective photothermolysis: Precise microsurgery by selective absorption of pulsed radiation," Science, vol. 220, pp. 524-527, Apr. 1983.

Anderson, R.R. et al., "The optics of human skin," Journal of Investigative Dermatology, vol. 77, No. 1, pp. 13-19, 1981.

Apfelberg et al. "Analysis of Complications of Argon Laser Treatment for Port Wine Hemangiomas with Reference to Striped Technique," Lasers in Surgery and Medicine, 2:357-371 (1983).

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).

Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.

Bjerring, P. et al., "Selective Non-Ablative Wrinkle Reduction by Laser," J Cutan Laser Ther, vol. 2, pp. 9-15, 2000.

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Catalogue ILC, "High Performance flash and arc lamps," Book 3, 3rd edition.

Chan, E.K., "Effects of Compression on Soft Tissue Optical Properties," IEEE Journal of Selected Topics in Quantum Electronics, vol. 2, No. 4, pp. 943-950 (Dec. 1996).

Dabrowska, "Intravital Treatment of the Pulp with Stimulation Laser Biostimulation," Abstract Rocz-Akad-Med-Bialymst. 1997; 42(1): 168-76.

Dixon et al. "Hypertrophic Scarring in Argon Laser Treatment of Port-Wine Stains," Plastic and Reconstructive Surgery, 73:771-777 (1984).

Doukas et al., "Transdermal Drug Delivery With a Pressure Wave," Advanced Drug Delivery Reviews 56 (2004), pp. 559-579.

Dover, J.S. et al., "Pigmented guinea pig skin irradiated with Q-switched ruby laser pulses," Arch Dermatol, vol. 125, pp. 43-49, Jan. 1989.

European Search Report, European Patent Application No. 1 0012969.1, Dated Jul. 13, 2011.

Finkelstein, L.H. et al., "Epilation of hair-bearing urethral grafts using the neodymium:yag surgical laser," Journal of Urology, vol. 146, pp. 840-842, Sep. 1991.

Fiskerstrand, E.J. et al., "Hair Removal with Long Pulsed Diode Lasers: A Comparison Between Two Systems with Different Pulse Structures," Lasers in Surgery and Medicine, vol. 32, pp. 399-404, 2003.

Forrest-Winchester et al., "The Effect of Infrared Laser Radiation on Dentinal Permeability in vitro," Department of Dentistry, University of Queensland Dental School, pp. 1-8, 1992.

Ginsbach et al. "New Aspects in the Management of Benign Cutameous Tumors," Laser 79 Opto-Electronics, Munich Conference Proceedings, 344-347 (1979).

Goldman, L. et al. "Treatment of basal cell epithelioma by laser radiation," JAMA, vol. 189, No. 10, pp. 773-775.

Goldman, L. et al., "Effect of the laser beam on the skin, III. Exposure of cytological preparations," Journal of Investigative Dermatology, vol. 42, pp. 247-251, 1964.

Goldman, L. et al., "Effect of the laser beam on the skin, Preliminary report" Journal of Investigative Dermatology, vol. 40, pp. 121-122, 1963.

Goldman, L. et al., "Impact of the laser on nevi and melanomas," Archives of Dermatology, vol. 90, pp. 71-75, Jul. 1964.

Goldman, L. et al., "Laser action at the cellular level," JAMA, vol. 198, No. 6, pp. 641-644, Nov. 1966.

Goldman, L. et al., "Laser treatment of tattoos, A preliminary survey of three year's clinical experience," JAMA, vol. 201, No. 11, pp. 841-844, Sep. 1967.

Goldman, L. et al., "Long-term laser exposure of a senile freckle," Arch Environ Health, vol. 22, pp. 401-403, Mar. 1971.

Goldman, L. et al., "Pathology, Pathology of the effect of the laser beam on the skin," Nature, vol. 197, No. 4870, pp. 912-914, Mar. 1963.

Goldman, L. et al., "Preliminary investigation of fat embolization from pulsed ruby laser impacts of bone," Nature, vol. 221, pp. 361-363, Jan. 1969.

Goldman, L. et al., "Radiation from a Q-switched ruby laser, Effet of repeated impacts of power output of 10 megawatts on a tattoo of man," Journal of Investigative Dermatology, vol. 44, pp. 69-71, 1965.

Goldman, L. et al., "Replica microscopy and scanning electron microscopy of laser impacts on the skin," Journal of Investigative Dermatology, vol. 52, No. 1, pp. 18-24, 1969.

Goldman, L. et al., "The biomedical aspects of lasers," JAMA, vol. 188, No. 3, pp. 302-306, Apr. 1964.

Goldman, L. et al., "The effect of repeated exposures to laser beams," Acta derm.-vernereol., vol. 44, pp. 264-268, 1964.

Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

Goldman, L., "Effects of new laser systems on the skin," Arch Dermatol., vol. 108, pp. 385-390, Sep. 1973.

Goldman, L., "Laser surgery for skin cancer," New York State Journal of Medicine, pp. 1897-1900, Oct. 1977.

Goldman, L., "Surgery by laser for malignant melanoma," J. Dermatol. Surg. Oncol., vol., 5, No. 2, pp. 141-144, Feb. 1979.

Goldman, L., "The skin," Arch Environ Health, vol. 18, pp. 434-436, Mar. 1969.

Goldman, L., Biomedical Aspects of the Laser, Springer-Verlag New York Inc., publishers, Chapts. 1, 2 & 23, 1967.

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

US 6,230,044, 05/2001, Afanassieva et al. (withdrawn)

* cited by examiner

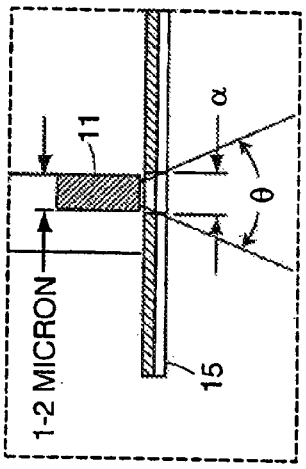
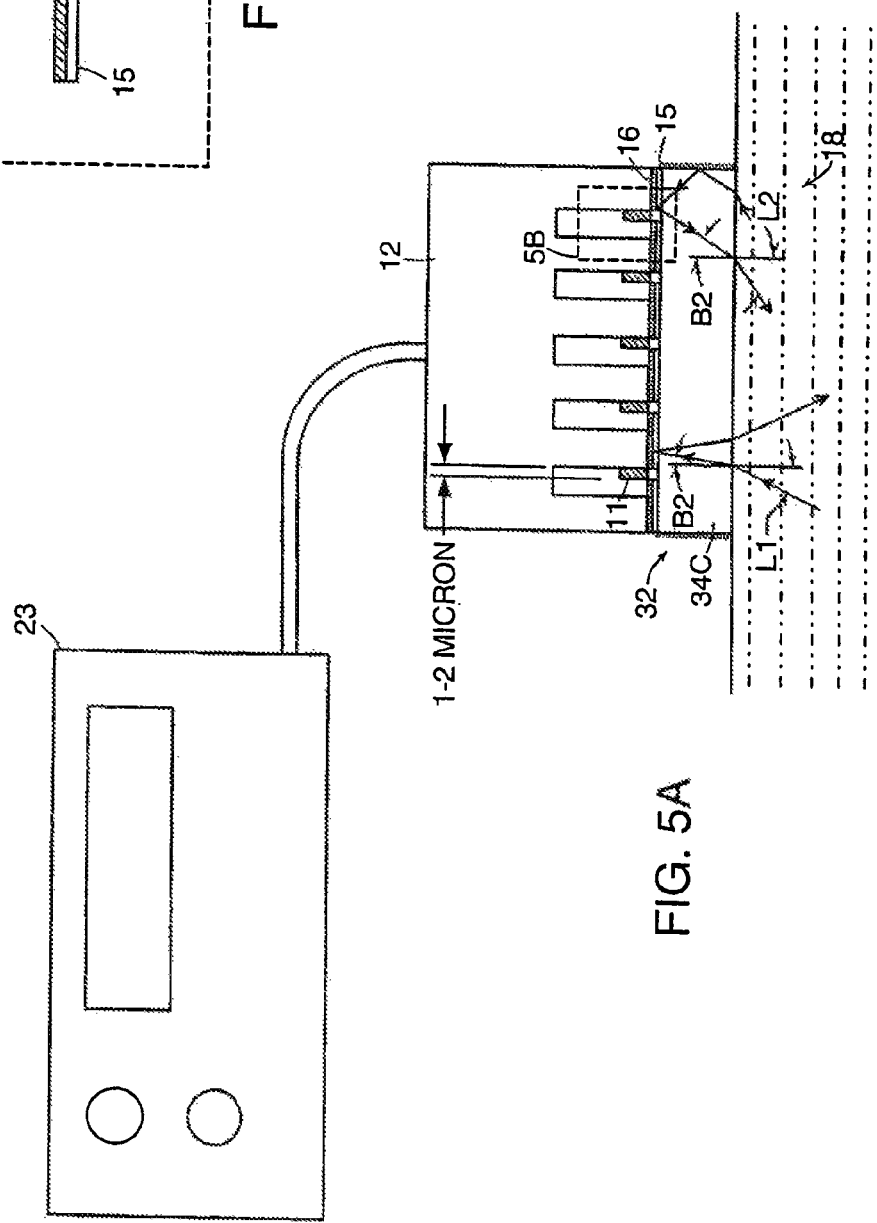
FIG. 5B
FIG. 5A

LIGHT ENERGY DELIVERY HEAD

PRIOR APPLICATIONS

This application is a continuation of application Ser. No. 12/840,513, filed Jul. 21, 2010, which is a continuation of application Ser. No. 11/301,340, filed Dec. 12, 2005, now U.S. Pat. No. 7,763,016, which is a continuation of application Ser. No. 10/738,738, filed Dec. 16, 2003, now U.S. Pat. No. 6,974,451, which is a continuation of Ser. No. 10/052,474, filed Jan. 18, 2002, not U.S. Pat. No. 6,663,620, which is a continuation of application Ser. No. 09/473,910, filed Dec. 28, 1999, now U.S. Pat. No. 6,517,532, which claims priority from provisional application Nos. 60/115,447 filed Jan. 8, 1999 and 60/164,492, filed Nov. 9, 1999, and which is also a continuation-in-part of application Ser. No. 09/078,055, filed May 13, 1998, now U.S. Pat. No. 6,273,884, which application claims priority from provisional application Nos. 60/077,726, filed Mar. 12, 1998 and 60/046,542, filed May 15, 1997. The contents of all of these prior applications are incorporated herein by reference in their entireties.

FIELD OF THE INVENTION

This invention relates to light energy delivery heads, and more particularly to a laser diode head or other light energy delivery head for delivering light energy to a selected depth in a medium, particularly a scattering medium, which head provides improved heat management for both the laser diodes (or other light energy emitter) and the medium and/or which more efficiently utilizes light energy from the laser/emitter.

BACKGROUND OF THE INVENTION

Light energy emitters, including lasers, and in particular semiconductor diode lasers, flash lamps, halogen and other filament lamps, etc., are finding increasing application in medical, industrial, research, governmental and other applications. For many of these applications, the light energy is to be delivered at a selected depth in a light scattering medium. Because of the scattering, only a fraction of the light energy delivered to the surface of the medium reaches the target area, with much of the remaining energy being refracted out of the medium and dissipated in the surrounding atmosphere. For a highly scattering medium such as skin, as much as 50-80 percent of the incident energy may be lost due to this back scattering effect, requiring more powerful light energy emitters/lasers or a larger number of emitters/diodes lasers (where diode lasers are used), or requiring that light energy be delivered over a much smaller area, in order to achieve a desired fluence at a target. Utilizing a head with a more powerful emitter/laser or utilizing a larger number of and/or more powerful emitters/diode lasers makes the head larger and more expensive and increases the heat management problems resulting from use of the head. Concentrating the beam to achieve higher fluence with smaller spot size or aperture adversely affects the depth in the medium which can be reached by the light energy and can significantly increase the time required to perform a given procedure.

U.S. Pat. No. 5,824,023, to Rox Anderson, teaches one way of dealing with the reflection problem with certain laser or other light energy emitting devices. However, the technique of this patent also results in small spot sizes and is not readily adaptable for use in certain applications, such as in laser diode heads. An improved technique is therefore required to permit optimum utilization of the light energy from light energy emitting devices in general, and from laser diodes or laser diode bars of a laser diode head in particular, by recycling or reusing light scattered from the surface of the irradiated medium and directing it back toward a desired target area in the medium.

A related problem involves heat management when using a laser diode head, or other head containing light energy emitters, and in particular the ability to utilize a common cooling element to cool both the laser diodes/light energy emitters and the surface of the medium being irradiated. Surface cooling can be required in various applications, particularly medical applications, since laser energy being delivered at a depth in the medium, for example a patient's skin, must pass through the surface of the medium, for example the epidermis of a patient's skin, in order to reach the target area. Heating of the medium surface can cause damage at the surface if suitable cooling is not provided. Prior art systems have either not provided cooling for the medium surface or have required separate cooling elements for the diodes and the medium.

SUMMARY OF THE INVENTION

In accordance with the above, this invention provides, in a first aspect, a head for applying light energy to a selected depth in a scattering medium having an outer layer in physical and thermal contact with the head. The head includes a thermally conductive block or mount having an energy emitting surface; at least one laser diode or other energy emitting element mounted in the block adjacent the energy emitting surface, each of the elements being in thermal contact with the mount and being oriented to direct light energy through the energy emitting surface. A thin, transparent, thermally conductive layer is provided over the light emitting surface and in thermal contact therewith, the layer being in contact with the outer layer of the medium when the head is applying light energy thereto. Finally, a cooling mechanism is provided for the mount, permitting the mount to sink heat from both the elements and the outer layer of the medium. For some embodiments, the thermally conductive layer is a coating formed on the light emitting surface of the mount.

For preferred embodiments, the head also includes a reflecting layer formed on the thermally conductive layer, which reflecting layer has an opening formed therein under each element through which light energy may be applied to the medium. The reflecting layer is preferably between the thermally conductive layer and the energy emitting surface of the mount/block, and preferably has an area larger than the area of the block. In particular, the area of the reflecting layer could be at least substantially as large as the aperture of reflection for scattered light energy from the medium. In order to achieve a desired amplification coefficient (f) as a result of retroreflection from the reflecting layer, the aperture through which light energy is applied to the medium should have a minimum dimension $$D_{min} = \frac{d}{\sqrt{\frac{f \cdot R \cdot r}{f-1}} - 1}$$

where d is a back-scatter aperture increment for a given wavelength and medium, R is the reflection coefficient of the medium and r is the reflection coefficient of the reflecting layer.

The block for the laser diode head may assume a variety of forms. In particular, for some embodiments of the invention, the block has a depression formed therein, with the energy emitting surface being the surface of the depression, and with each of the elements for some embodiments being mounted to emit light energy substantially perpendicular to the depression surface at the point thereon where the element is mounted. The medium is forced into the depression and into contact with the surface thereof. The forcing of medium into the depression may be accomplished by merely pressing the head against a soft deformable medium, such as some areas of a person's skin, or suction, for example a vacuum line, may be provided to draw the skin or other medium into the depression. The depression may have a variety of shapes, including being substantially semi-cylindrical or substantially rectangular. Where the head is being utilized for hair removal on for example a person, the depression may be of a size sufficient to permit a single hair follicle to enter the depression in the plane of the rectangular depression.

The reflecting layer may also be formed and utilized for heads which use the cooled block to cool the diodes or other light energy emitters only and not to cool the surface of the medium, for example in applications where a thicker transparent layer is employed or for heads using light energy emitting elements other than laser diode bars, for example filament lamps or light pipes fed by a suitable light emitting component. For such heads, the reflecting layer would still have areas of the type indicated above and would preferably have an emitting aperture with a minimum dimension $D_{min}$ determined as indicated above. For these embodiments, the transparent layer could be a waveguide of selected shape, which shape could be a truncated shape which, depending on desired aperture size, would have either its larger end or shorter end adjacent the block. Selected sides or walls of the waveguide may have an angle dependent reflecting layer to attenuate sharply angled light energy entering the waveguide.

In still another aspect of the invention, the head may include at least one energy emitting element mounted to apply light energy to the medium through an aperture, which aperture has a minimum dimension $D_{min}$ defined as indicated above, and a reflecting layer mounted to retroreflect light energy back-scattered from the medium. The aperture may be circular, with D being a diameter of the aperture, or substantially rectangular, with D as the length of a short side of the aperture.

The foregoing and other objects, features and advantages of the invention will be apparent from the following more specific description of preferred embodiments of the invention as illustrated in the accompanying drawings.

BRIEF DESCRIPTION OF THE DRAWINGS

FIG. 5A is a cutaway, side elevation, semi-schematic representation of a third species of the second embodiment of the invention, FIG. 5B being an enlarged, side elevation view of a portion of the species shown in FIG. 5A;

DETAILED DESCRIPTION

Figure 1:
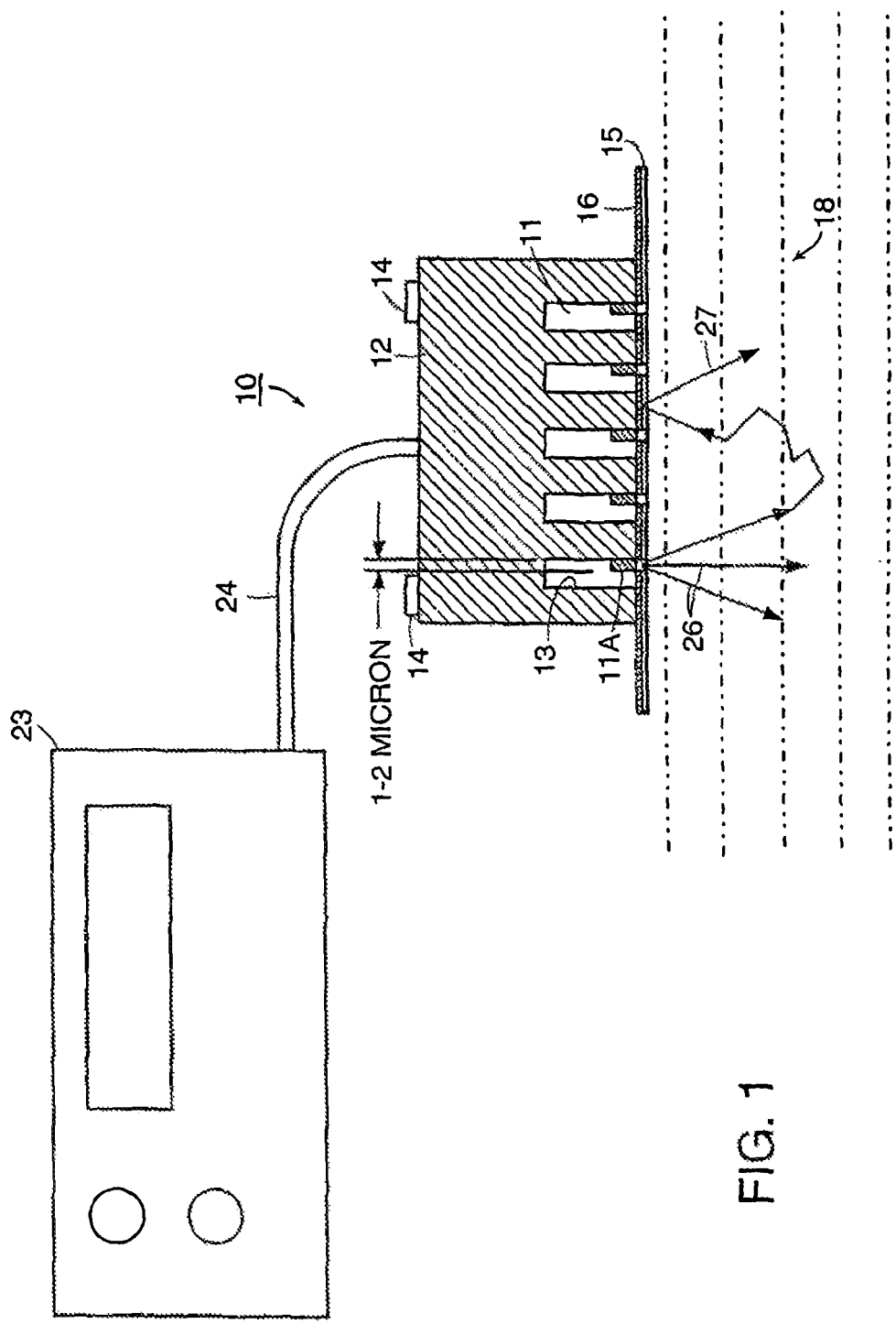
FIG. 1 is partially cutaway, side elevation, semi-schematic representation of a head in accordance with a first embodiment of the invention.

Referring first to FIG. 1, a laser head 10 is shown which contains a plurality of laser diode bars 11, each of which includes a plurality of emitters 11A and is mounted in a groove 13 formed in a block 12. Block 12 may be formed of one or more materials having good thermal conduction properties, and may be fabricated in a number of ways, all of which are within the contemplation of this invention. In particular, block 12 may be formed of a single material which, in addition to having good thermal conduction properties, is also an electrical insulator, with the side walls of grooves 13 being coated or plated with an electrically conducting material and the diode bars soldered in the grooves, an electrical circuit being formed between adjacent grooves so that current may flow through the diodes without being shorted through block 12. Alternatively, the portion of block 12 between grooves 13 may be fabricated of electrically conductive mounts which are secured in a suitable way to a thermally conducting and electrically insulating substrate, the conducting mounts providing an electrical path through the diodes and the insulating substrate preventing shorts. Other techniques for providing an electrical path through the diodes to permit selective energization thereof, while not provided a short circuit path through block 12 may also be employed.

Block 12 serves as a heat sink for diode bars 11 and a variety of techniques may be utilized to remove heat from block 12. These include providing one or more channels through block 12 and flowing a fluid, which is generally water but may be some other liquid or gas, through the channel to remove heat from block 12. Alternatively, one or more thermo-electric components 14, for example Peltier elements, may be attached to block 12 and utilized to remove heat therefrom.

A transparent element 15 having a high reflectivity mask 16 attached thereto is mounted to the bottom of block 12, with mask 16 preferably being between block 12 and element 15. For a preferred embodiment where head 10 is being used for dermatological treatment, the scattering media 18 being the skin of a patient, the transparent element is preferably formed of sapphire or some other material having a good index match with skin, and is preferably either a sapphire coating which is for example 1 to 2 microns thick, or a sapphire plate or wafer which is for example 1 to 2 mm thick. If component 15 is a plate or wafer, then mask 16 may be a coating of a highly reflective material such as Ag, Cu, Au or a multilayer dielectric coating which is formed using an appropriate coating technology known in the art, such as lithography, on the plate/wafer 15. Openings 20 (FIG. 2A) are formed in the coating 16 under each of the diode bar emitter 11A, the openings 20 being only large enough to permit light from the diode bars to pass unobstructed therethrough. Keeping slits or openings 20 in reflective layer or mask 16 as small as possible is desirable in that it maximizes the reflectivity of the mask and thus, as will be discussed later, optimizes retroreflection of scattered energy from skin or other media 18. For reasons which will be discussed in greater detail later, reflective layer 16 should have a larger footprint than block 12 to further enhance the reflection back into the media 18 of scattered light or energy emitted therefrom. Since for the illustrative embodiment, mask 16 is supported on transparent plate or wafer 15, this component also has a larger profile. Alternatively, mask 16 may be a thin plate or wafer having slits 20 formed therein, and transparent component 15 may be a layer of for example sapphire having a thickness in the 1 to 2 micron range which is coated thereon. In this case, the coating need not extend beyond the dimensions of block 12; however, it is preferable that this coating extend for the full dimensions of mask 16 to provide a good optical index match for retroreflected light.

Finally, the apparatus of FIG. 1 includes a box 23 connected to head 10 by suitable electrical lines and, where appropriate, plumbing lines (for cooling water) 24. Box 23 may contain appropriate power supplies for diodes bars 11, control circuitry, fluid pumps where fluid cooling is utilized and other appropriate components. The specific components contained in box 23 do not form part of the present invention.

The apparatus of FIG. 1 has several advantageous features over the prior art. First, where the medium 18 is the skin of a patient undergoing a dermatological procedure, such as for example the removal of a tattoo, a port wine stain, blood vessel, or other vascular lesion, or hair removal, it is desirable to cool the epidermis, the surface layer of the skin, to prevent thermal damage thereto during the procedure. In the prior art, a cooling mechanism has been provided for the epidermis in particular, and for the surface area of a patient's skin in general, which cooling mechanism is separate and independent from the cooling mechanism utilized to sink heat from diode bars 11. These separate cooling mechanisms add to the size, weight, complexity and cost of the system in general, and of the delivery head 10 in particular. The embodiment of FIG. 1 overcomes these problems by having at most a few millimeters of material between the block 12, which is cooled by thermoelectric components 14, by a flowing fluid, and/or by other suitable means, and the patient's skin. Further, the sapphire typically used for transparent component 15 has good thermal transfer properties so that heat from the patient's skin may easily flow to cooled block 12, and this block may serve as a heat sink for both diode bars 11 and the epidermis of a patient's skin or other surface area of a media 18 to which light energy is being applied. This arrangement is more compact, simpler and less expensive than prior art heads performing the same function.

Further, as illustrated in the Figure, light energy emitted from a diode bar 11 in the form of rays 26 is scattered in media 18, for example in a patient's skin, and at least some of this energy, perhaps 70 percent, depending on the pigmentation of the patient's skin, is reflected back and exits the patient's skin at some angle. Substantially all of this light impinges on reflecting surface or mask 16, and, since this mask has a reflectivity approaching 100 percent, substantially all of this light energy is retroreflected back into the skin. This retroreflection results in a roughly 300 percent increase in the light energy or fluence reaching a target at a selected depth in the patient's skin for a given fluence emitted from diode bars 11.

This means that either the same therapeutic results can be achieved using less diode bars 11 or lower energy diode bars 11 or that higher energy, and therefore more effective treatment, can be achieved using the same number and power of diode bars. More effective results can thus be achieved for a given size, cost and complexity of the diode laser head.

Figure 10B:
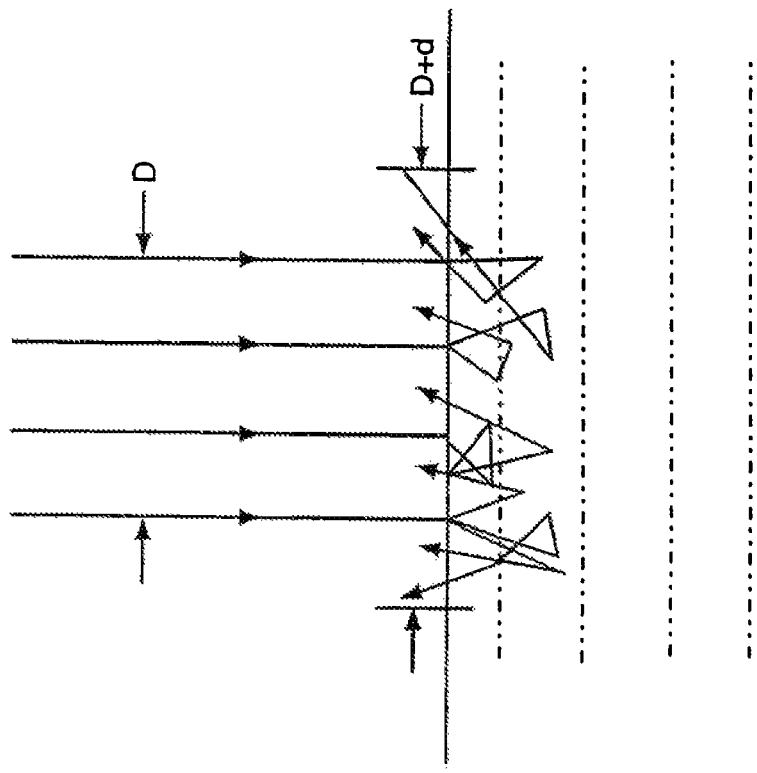
FIGS. 10A and 10B are graphic representations illustrating the back scattering effect for a narrow and a wide beam respectively.
Figure 10A:
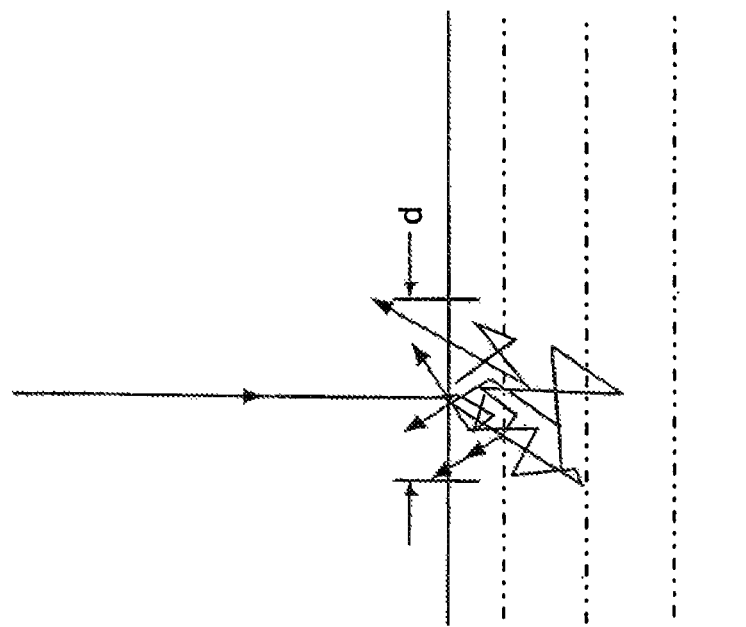

Further, as illustrated in FIG. 10B, light energy entering scattering medium 18 over an aperture of size D will, because of beam divergence and scattering, exit the medium over an aperture D+d, where d is a back-scatter aperture increment and is substantially constant for a given beam wavelength and medium, regardless of the input aperture D. This is illustrated by FIGS. 10A and 10B, where d is substantially the same for a thin beam which substantially enters the medium 18 at a single point and for a wide beam having an aperture D. Thus, as the aperture size D increases, d becomes a smaller percentage of the reflection aperture D+d. For a generally circular aperture, D and D+d are diameters, while for a generally rectangular aperture, these values may be considered to be the length of the smaller side of the rectangle.

The reflection by reflective mask 16 can increase the amount of energy reaching a desired target area by several times. This increase in effective usage of light energy can be quantitatively described by the increase in illumination inside scattering medium 18, this increase being the ratio (f) between the illumination at an arbitrary target point inside the scattering medium when the reflected light is returned back to the medium ($I_R$) and when it is not ($I_O$) (i.e., $f=I_R/I_O$). The value of f depends on the reflectance coefficient R of the scattering medium 18 and the coefficient of reflection of the reflecting mask 16 (r) which returns the scattered light back into the medium (i.e., f=1/1−Rr). However, this known dependence does not take into account the influence of beam aperture D; since the beam aperture increases by d as a result of scattering, amplification coefficient f has a strong dependence on the aperture D of the incident beam. In particular, in accordance with the teachings of this invention, it has been determined that when beam aperture is taken into account, the amplification coefficient f can be approximated by the following equation:

$$f = \frac{1}{1 - Rr\left(\frac{D/d}{1+D/d}\right)^2} \quad (1)$$

Using equation 1 for a given medium, a given reflector, and a desired illumination amplification, a minimum beam aperture ($D_{min}$) can be determined. $D_{min}$ is generally given by:

$$D_{min} = d \cdot \frac{1}{\sqrt{\frac{\sqrt{f \cdot R \cdot r}}{f-1}} - 1} \quad (2)$$

For f=2, this minimum reduces to $$D_{min} = d \cdot \frac{1}{\sqrt{2 \cdot R \cdot r} - 1} \quad (3)$$

Figure 11:
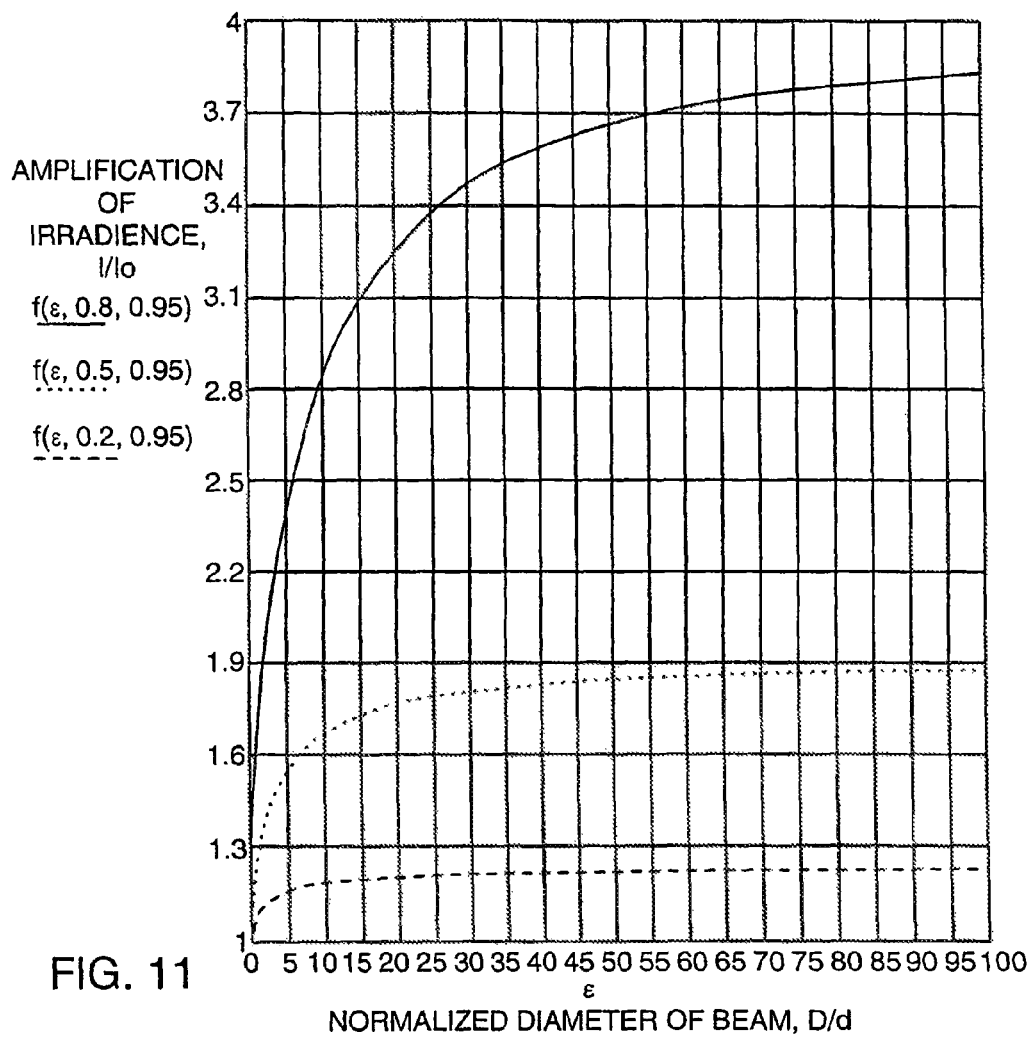
FIG. 11 is a graphic representation of the relationship between a coefficient for amplification of irradiance in a scattering medium and beam diameter for three mediums having different diffuse reflecting characteristics.

With light skin as a reflecting medium, and an incident beam in the red region of the spectrum, the values in the above equation would be R≈0.7 and d≈3 mm. Assuming a reflector with r≈0.95 would then result in a $D_{min}$=19.5 mm. This suggests that for most applications in laser dermatology, the beam diameter or other appropriate dimension (D) should be greater than 20 mm in order for retroreflection to provide desired illumination amplification. This is illustrated in FIG. 11 where (f) is shown as a function of the ratio D/d for three reflection environments, with r being 0.95 in each instance, and with R equaling 0.2, 0.5 and 0.8, respectively. It is seen that, particularly for the highly scattering medium having R=0.8, f continues to increase with increasing input aperture size and may, with retroreflection, provide up to 3.8 times the intensity achieved without retroreflection. Assuming d is equal to 3 mm, an input aperture of 20 mm would result in well over two times the illumination at the target than if retroreflection were not utilized, and a smaller aperture, for example D=15 mm, would still provide significant amplification. Thus, while each individual diode bar 11 produces a beam having a dimension in the micron range, head 10 can be designed to provide a beam having a dimension D which is sufficient to provide a desired illumination amplification. The reflecting surface 16 is preferably made large enough so as to fully cover the reflection aperture which consists of D+d, but may require little or no extension beyond the end of block 12 where D is large relative to d.

The embodiment shown in FIG. 1 thus provides at least three significant advantages over prior art laser diode heads. First, it provides a very efficient mechanism for cooling both the laser diodes and the surface of medium 18 by use of the same cooling mechanism. Second, it provides a simple and effective mechanism for retroreflecting light scattered from medium 18 over the entire scattering aperture from such medium; and third it provides a beam aperture which is large enough for efficient illumination amplification as a result of retroreflection while using radiation sources, for example laser diode bars, which individually provide small beam apertures in the micron range.

Figure 2B:
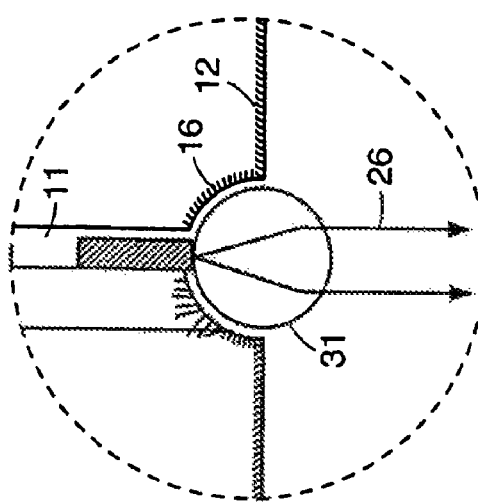
FIGS. 2A and 2B are enlarged side elevation views of a portion of the head shown in FIG. 1 for two different species thereof.
Figure 2A:
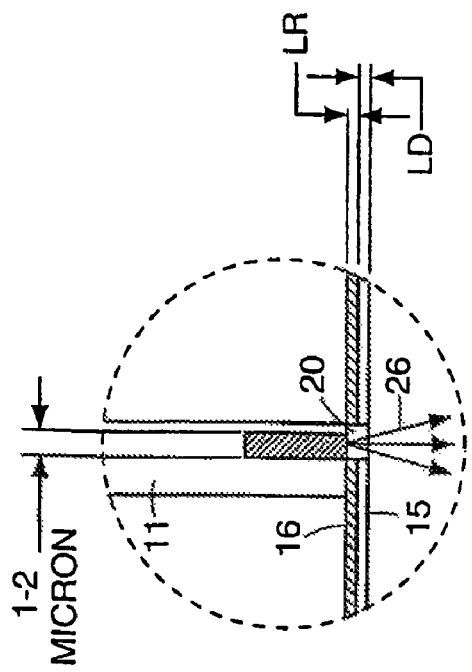

FIG. 2B illustrates an alternative embodiment of the invention which may be useful in some applications. The embodiment of FIG. 2B differs from that of FIG. 2A in that transparent layer 15 has been replaced by a cylindrical lens 31 mounted under each of the laser diode bars 11. Cylindrical lenses 31 can be supported to the array in ways known in the art including a support bracket or other support structure, either mounted to or forming part of block 12 at opposite ends of each cylindrical lens 31. Block 12 also extends somewhat below the bottom of diode bars 11 so as to supply structural support for lenses 31 and to permit block 12 to contact the upper surface of medium 18 when slight pressure is applied to block 12 so that the block may still function to cool the surface of the medium. A reflective coating 16 is formed on the bottom wall of block 12 in all areas thereof except the areas directly under diode bar emitters 11A, the reflective coating otherwise extending substantially around the entire wall of the recess in which lens 31 is positioned. Depending on its diameter, a lens 31 may function to collimate beam 26 emanating from the corresponding diode bar 11 into parallel rays, as opposed to diverging rays as shown in FIG. 2A, or to converge such beams toward a focal point which is preferably at the target depth. Such a collimating or converging of beam 26 reduces the ill effects of scattering on the beam, but does not eliminate such scattering or significantly reduce the need for reflective surface 16.

Figure 3B:
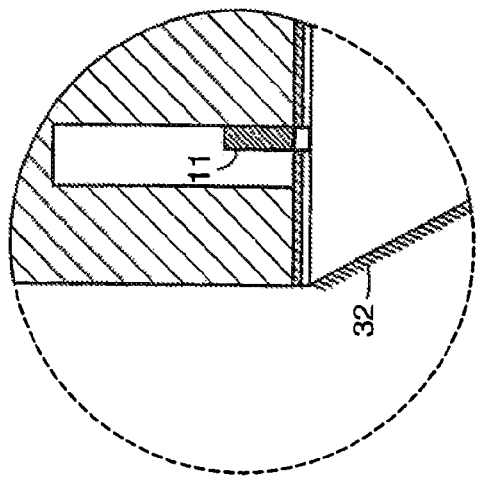
FIG. 3A is a cutaway, side elevation, semi-schematic representation of a head for a first species of a second embodiment, FIG. 3B being an enlarged side elevation view of a portion of the head shown in FIG. 3A.
Figure 3A:
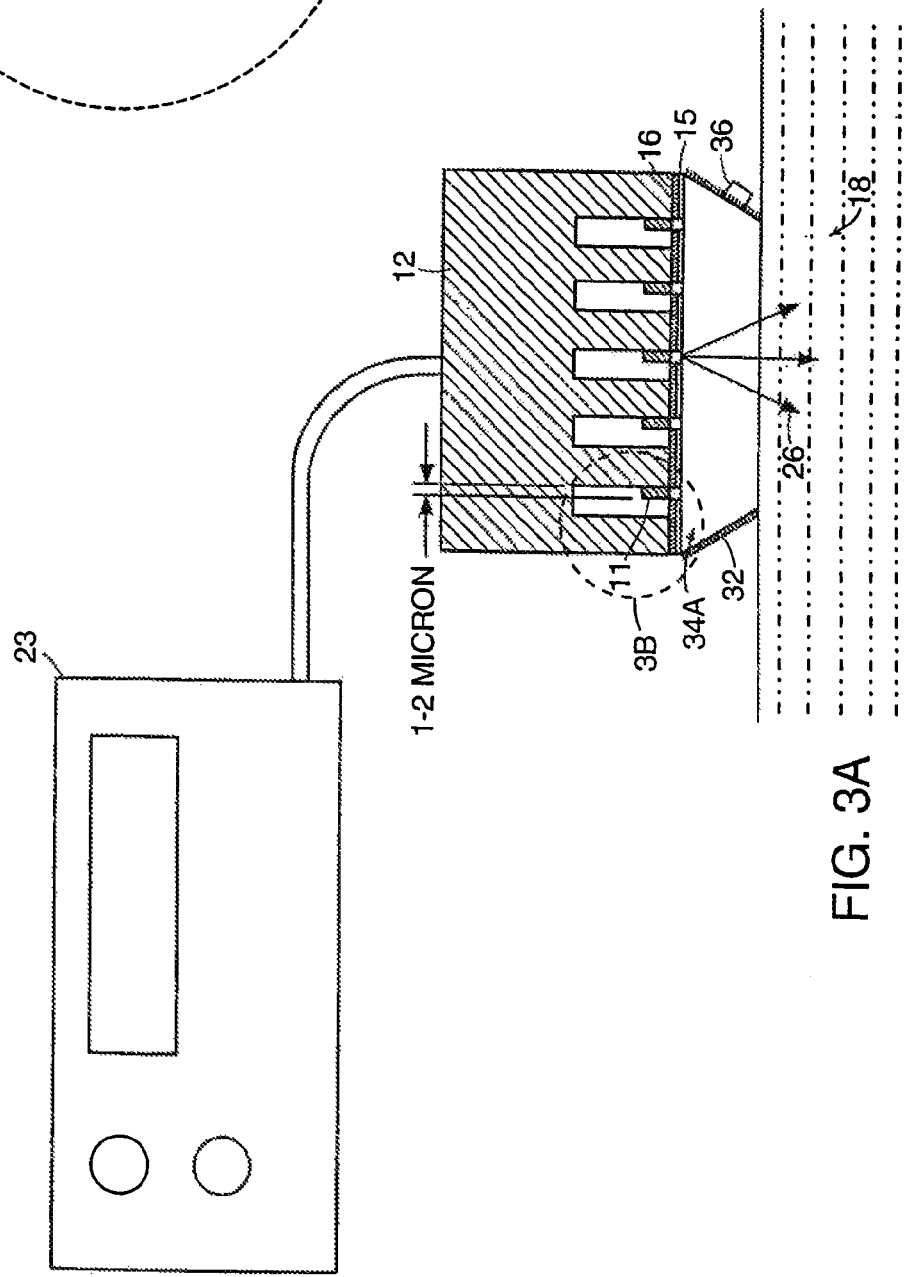

FIG. 3 shows an embodiment which differs from that of FIG. 1 in that higher fluence is required than is provided by the diode bars alone, even with retroreflection. Therefore, energy emitted from transparent layer 15 is applied to a standard concentrator 34A, which may be a hollow truncated cone or prism, but is preferably a block or slab of material having a good index match and good heat transfer properties to the medium 18, for example sapphire when the medium is human skin. Concentrator 34A sacrifices aperture size in order to achieve higher fluence in a manner known in the art. However, the aperture size is maintained sufficient to conform to the requirements specified in equation (2) above in order to maintain the energy amplification effects of retroreflection.

The embodiment of FIG. 3 also deals with a second problem in that scattered light is emitted from the skin at a variety of angles and is returned to the skin generally at the same angle received. This results in a higher concentration of optical energy at the surface of the skin where all beams are received and lower energy at depth, where the desired target is generally located, sharply angled beams only appearing at the surface. Since energy concentrated at the skin surface serves no useful therapeutic purpose and can cause thermal damage or discomfort if not adequately cooled, it is desirable to reduce or eliminate such sharply angled reflected beams, while not interfering with beams reflected at angles substantially perpendicular to the medium surface and returned to the skin at these angles. This objective is accomplished for the embodiment of FIG. 3 by providing a coating 32 on the side walls of concentrator 34A, which coating has angle-dependent reflection characteristics and may have significantly lower reflectivity than reflective surface 16. This means that the sharply angled beams impinging on surface 32 are attenuated or eliminated, thereby reducing the beams entering medium 18 at a sharp angle, these beams being only harmful and producing no useful therapeutic effect.

While the embodiment of FIG. 3 has the advantages discussed above, it also has two potential disadvantages. First, the aperture for receiving reflected radiation is smaller than the aperture (i.e., D+d) of reflected radiation, so that this embodiment does not collect all reflected radiation and retroreflect it to medium 18. This results in a slight decrease in the intensity amplification ratio (f) for this embodiment; however, this disadvantage is mitigated by the fact that much of the energy lost for this embodiment is energy at angles which, even if retroreflected, only contribute to heating the surface of medium 18 and do not to have a therapeutic effect or do other useful work at a target area located at a selected depth in the medium. D being larger than (d) also minimizes this loss. If desired, reflective extensions could also be provided for this embodiment to retroreflect all reflected energy.

The second disadvantage is that, depending on the thickness of concentrator 34A, cooled block 12 may not be effective for cooling the surface of medium 18. In particular, the time (t) it takes to remove heat from a slab of material having one side in good thermal contact with the surface to be cooled, an opposite side in good thermal contact with the cooling medium, in this case the block 12, and a distance or thickness (l) therebetween is given by:

$$t = l^2/\alpha \tag{4}$$

where $\alpha$ is the dielectric slab temperature conductivity coefficient. Where energy is being applied to the slab as successive laser pulses spaced by a time $t_p$, the slab thickness l for cooling to be affected is generally given by:

$$l < \sqrt{\alpha \cdot t_p} \tag{5}$$

Where the dielectric layer through which optical energy is transmitted and through which it is desired to perform cooling is formed of sapphire having a maximum $\alpha = 15 \cdot 10^{-6}$ m²/s, and for a typical interval between pulses of 0.25 s, this would result in the combined thickness for transparent layer 15 and concentrator 34A of less than 1.9 mm. Therefore, block 12 being utilized to cool both diode bars 11 and the surface of medium 18 would normally not be feasible when a concentrator 34A is utilized and, if cooling is required, it would normally be achieved by providing a separate cooling mechanism, for example one or more thermoelectric cooling elements 36, in contact with concentrator 34A, and preferably near the lower surface thereof. While only a single such cooling element is shown in FIG. 3, typically four or more such elements would be provided, spaced substantially evenly around the periphery of concentrator 34A, to provide uniform cooling thereof.

Figure 4:
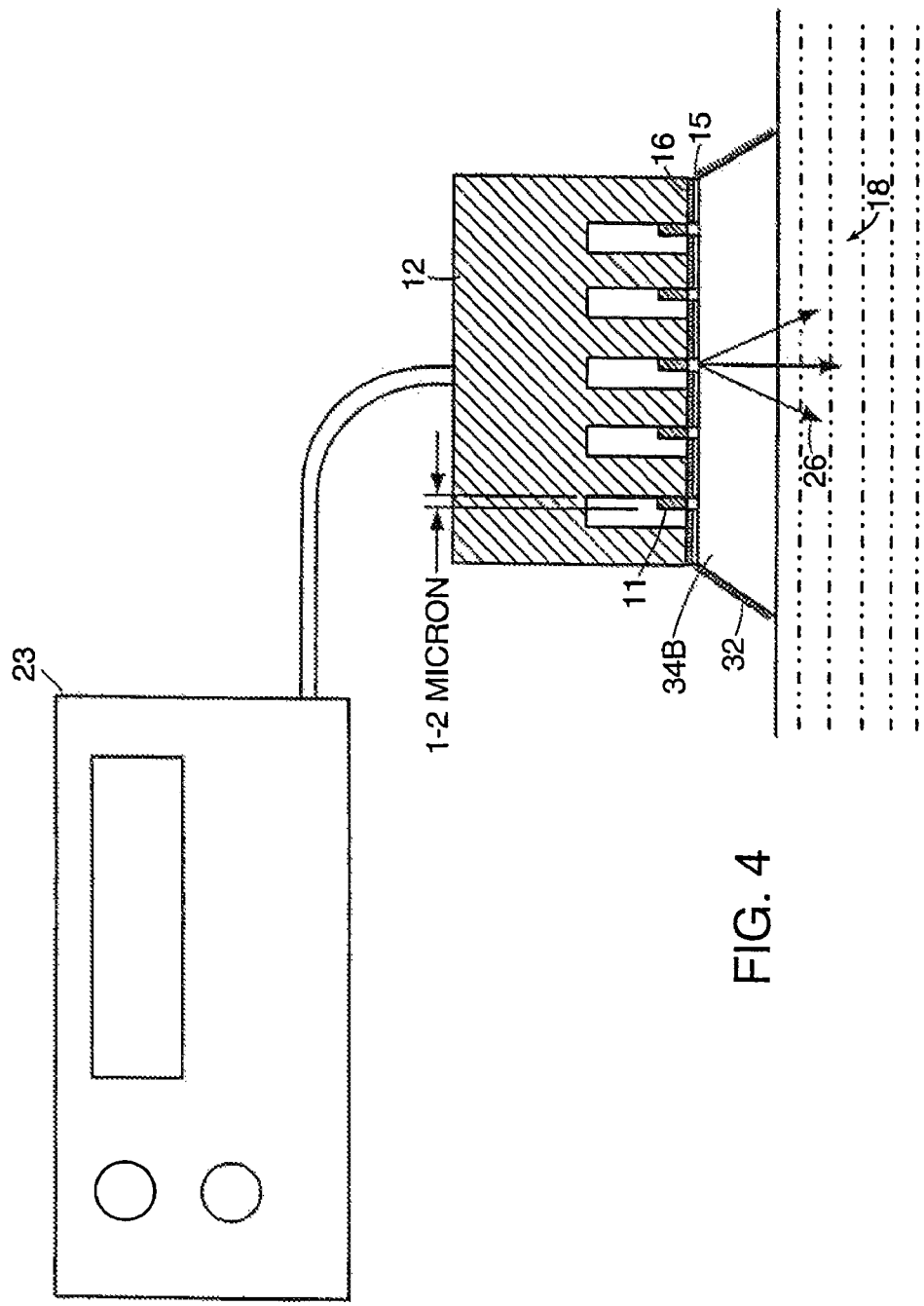
FIG. 4 is a cutaway, side elevation, semi-schematic representation of a second species of the second embodiment of the invention.

FIGS. 4 and 5 illustrate two additional embodiments of the invention which differ from that shown in FIG. 3 only in that, in FIG. 4, slab 34B is an expander rather than a concentrator, while in FIG. 5, slab 34C has parallel walls so as to not function either as a concentrator or an expander. Slabs 34A, 34B and 34C therefore permit a single block 12 with diode bars 11, transparent layer 15 and reflective layer 16 to be used to achieve a variety of programmable fluence levels. The embodiment of FIG. 4 is advantageous in that it permits more of the scattered light emitted from the surface of medium 18 to be collected and recycled than the other embodiments, with the embodiment of FIG. 5 having intermediate scattered light collecting capabilities. All three embodiments can have angle-dependent reflecting side walls 32 so as to reduce or substantially eliminate light being emitted at sharp angles. While the reduced reflection of surfaces 32 may be uniform, it is preferable that the reflectance from these surfaces be angle-dependent so that light impinging on these surfaces at sharper angles are more heavily attenuated, while light impinging on these surfaces at lesser angles, and therefore light which is more nearly emitted from the surface in a perpendicular direction, are attenuated much less, or in other words are more fully reflected. Further, reflecting surface 16 for all embodiments can also be angle-dependent, reflecting more strongly for light coming in at substantially perpendicular angles than for light coming in at sharper angles. While this may be achieved with a single layer coating, it is preferably achieved with a multilayer coating.

Figure 6:
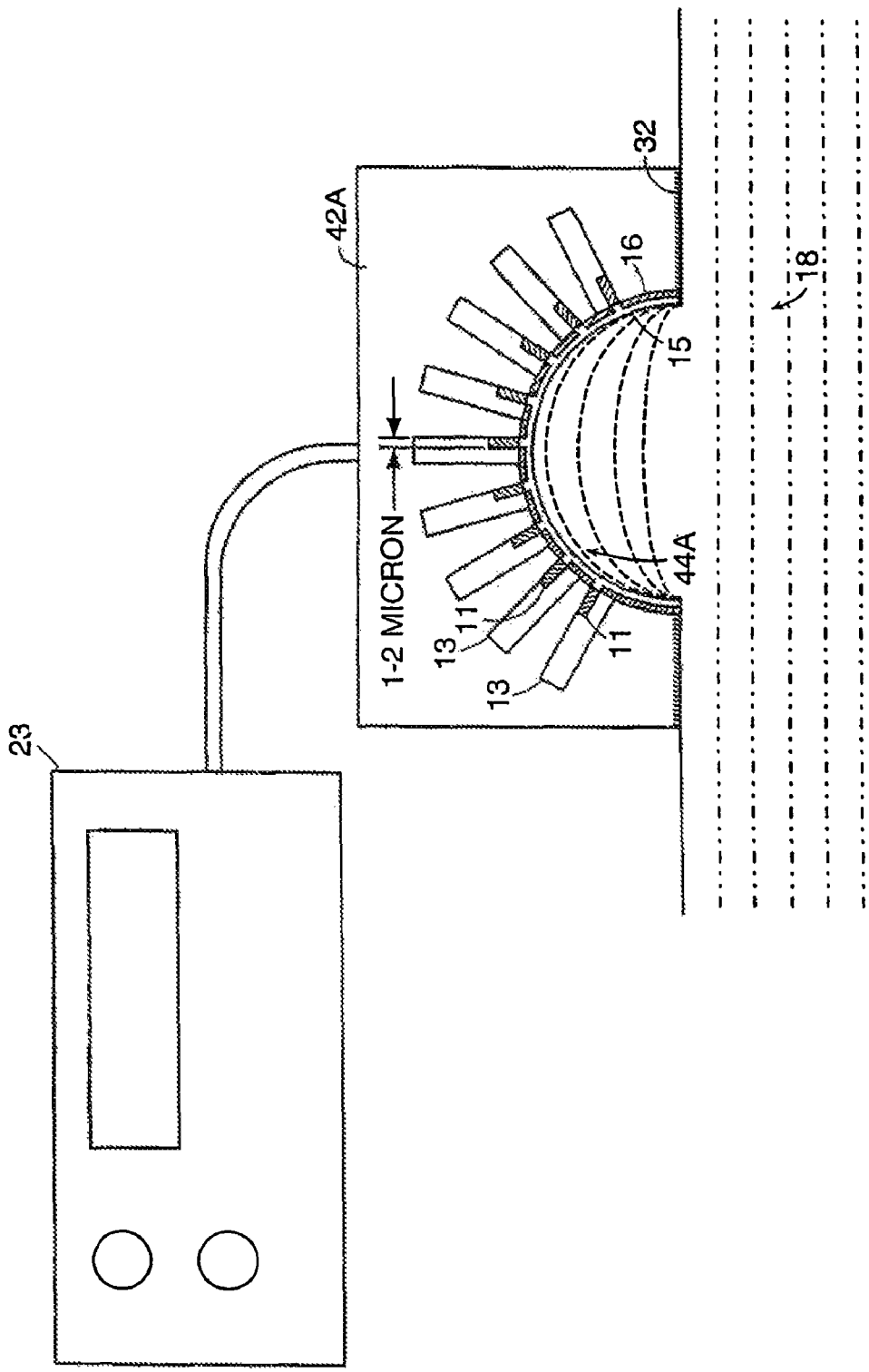
FIG. 6 is a cutaway, side elevation, semi-schematic representation of a first species for a third embodiment of the invention.
Figure 7:
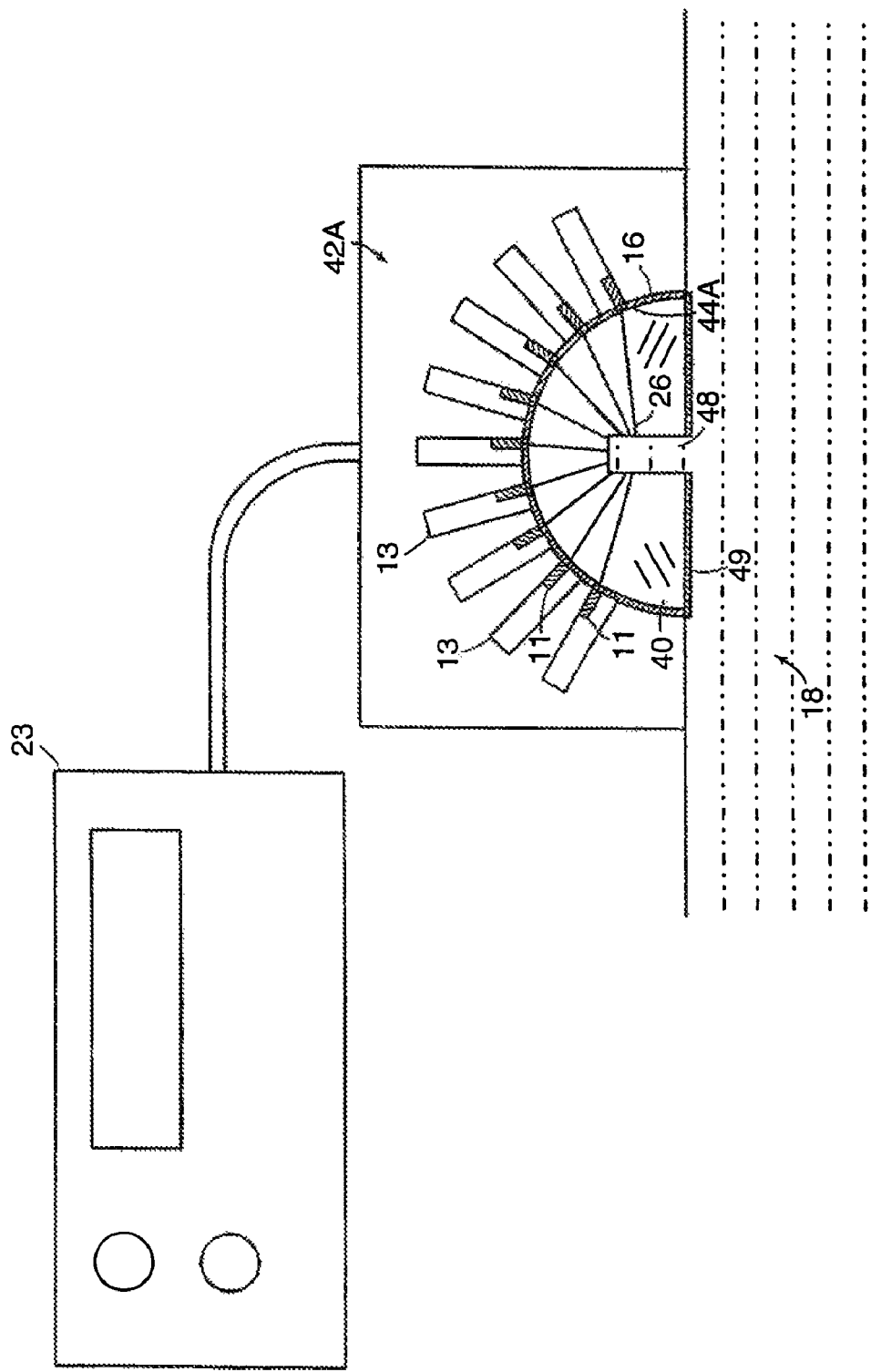
FIG. 7 is a cutaway, side elevation, semi-schematic representation of a second species for the third embodiment of the invention.
Figure 8:
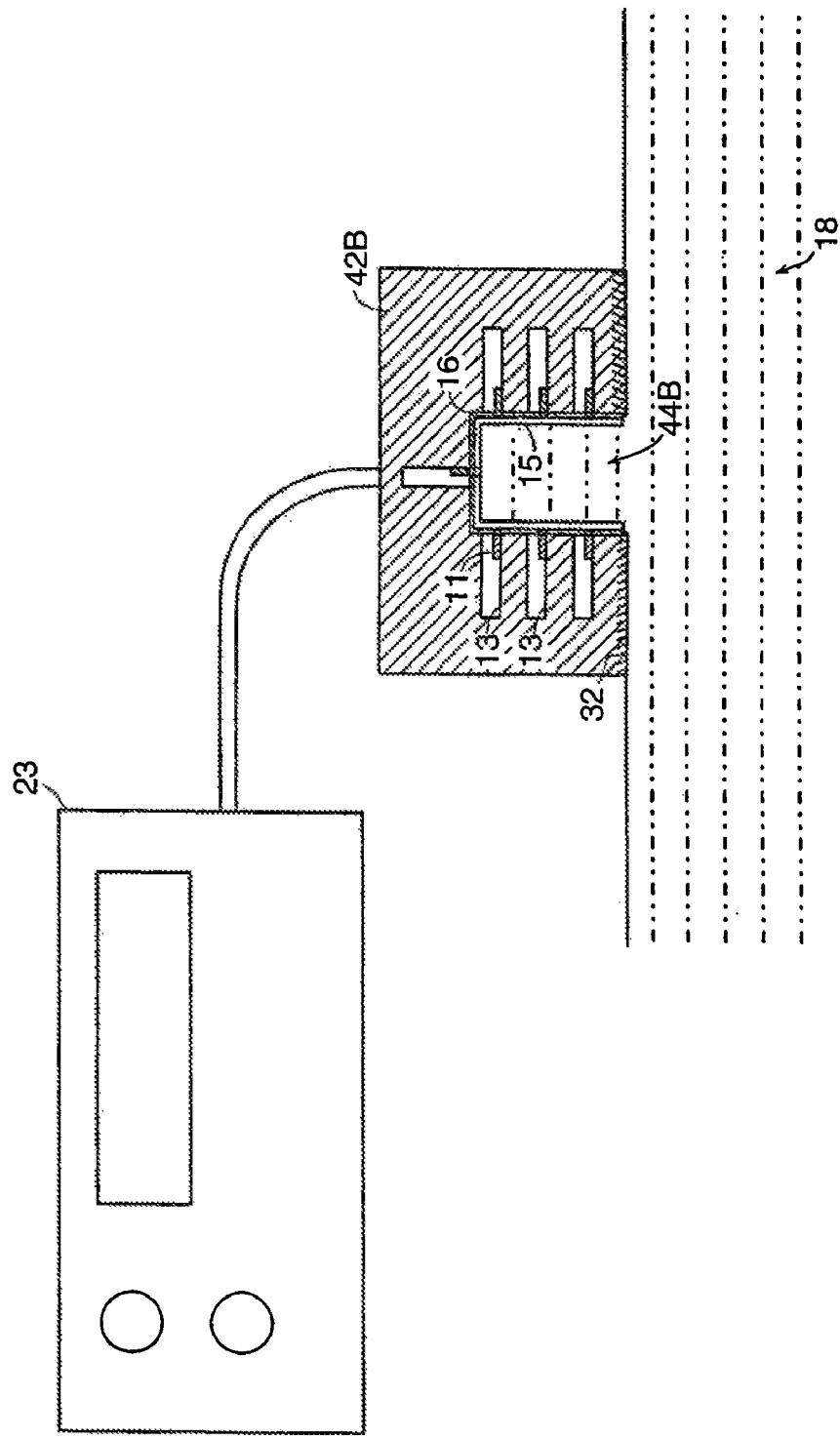
FIGS. 8 and 9 are cutaway, side elevation, semi-schematic representations of a third and fourth species of the third embodiment of the invention.

FIGS. 6-8 illustrate various species of still another embodiment of the invention wherein block 12 is replaced with a block 42 having a recess 44 formed therein. Grooves 13 are formed in a selected pattern around the perimeter of recess 44. In particular, referring to FIG. 6, the block 42A has a semi-cylindrical recess 44A formed therein with grooves 13 having diode bars 11 mounted therein being arranged in a semi-circular pattern around the periphery of recess 44A, each groove 13 and diode bar 11 therein being substantially perpendicular to the circumference of recess 44A (i.e., substantially parallel to a radii) at the point on the circumference where they are located. Part of the media 18 adjacent recess 44A is brought up therein and into contact with transparent surface 15 formed on the inside of the recess. Media may be brought into recess 44A either by pressing block 42A against a relatively soft media 18, for example skin in certain areas, to force the skin into the recess, or a source of vacuum may be provided, either adjacent the bars near the middle of the recess or between such bars, to pull the skin into the recess. Other techniques for forcing skin or other media 18 into the recess 44A may also be employed, either in addition to or instead of one or more of the two techniques mentioned above. Finally, the lower portion of block 42A outside of recess 44A has an angle-dependent reflective coating 32 formed thereon, this surface reflecting some light back into the skin in an area where it may be scattered to recess 44A.

For the embodiment of FIG. 6, the target area for the light energy would be at roughly the foci of the diode bars, which would generally be a point near the bottom center of recess 44A. Any light reflected by the skin prior to reaching such a target area would typically be reflected back into the recess and ultimately returned to the target resulting in a very high illumination increase ratio (f) for this embodiment.

FIG. 7 illustrates an embodiment which differs from that of FIG. 6 in that the recess 44A in block 42A, instead of merely having a thin transparent layer 15, has a transparent block or lens 40 positioned therein with a narrow rectangular recess 48 formed in cylindrical lens 40. Grooves 13 and the diode bars 11 mounted therein are at a slightly greater angle so as to have a focus near the upper middle of recess 48. The embodiment of FIG. 7 is particularly adapted for hair removal applications where a fold of skin having a single hair follicle in the plane of the Figure (there may be several hair follicles in the recess 48 along the length of the recess) is in recess 48 at a given time. Vacuum would normally be required to draw such a fold of skin into recess 48. As for the embodiment of FIG. 6, this embodiment results in a high concentration of light, including light reflected from reflecting surface 16 reaching the target point in recess 48. This effect is further enhanced by providing a highly reflective coating 49 on the bottom surface of cylindrical lens 40 which prevents light from exiting the lens into medium 18. Thus, substantially 100 percent of the light produced by diode bars 11 for this embodiment of the invention is applied to the target area, with virtually no energy being lost to scattering.

FIG. 8 is similar to FIG. 6 except that recess 44B in block 42B has a rectangular cross-section rather than a semi-circular cross-section, and grooves 13 are perpendicular to the walls of recess 44B at the points where they are located. While this embodiment does not result in a focusing of the light at a single point as for the embodiments of FIGS. 6 and 7, it does result in a high concentration of light energy in recess 44B which is applied to medium moved into the recess by pressure, vacuum, or other suitable means.

Figure 9:
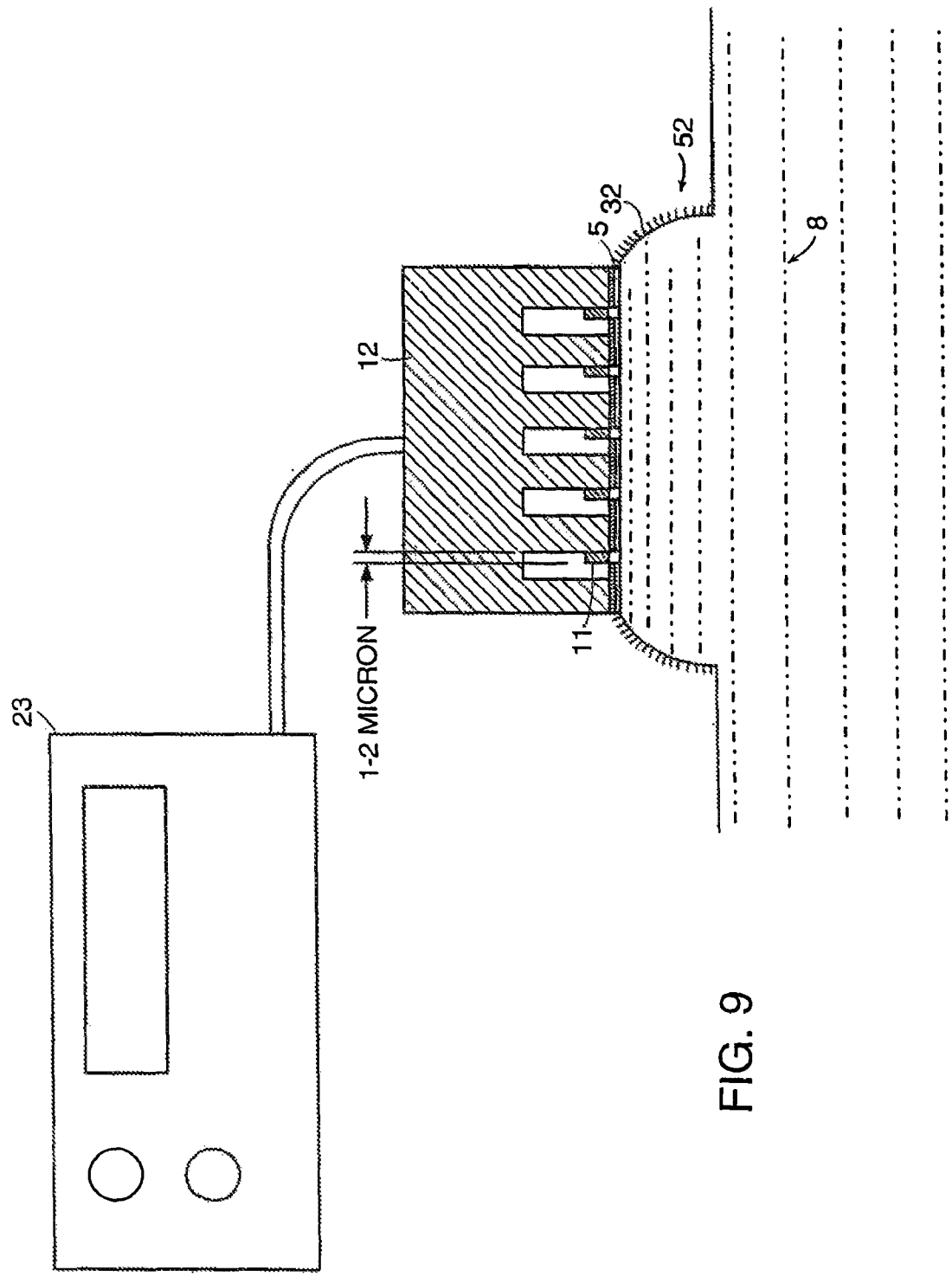

The embodiment of FIG. 9 is similar to that of FIG. 1 except that rather than there being extended portions for layers 15 and 16, there are flexible extensions 52 on each end of the block, which extensions have an angle-dependent reflective coating 32 formed thereon. Vacuum may be used to draw part of medium 18 into the area under block 12 and extensions 52 to provide enhanced radiation of a target area in this region or thereunder. The side sections 52 with angle-dependent reflective coating are more effective in directing light energy in the (d) region (FIG. 10B) into the target area than are the flanges of FIG. 1.

While not specifically mentioned above, the embodiments of FIGS. 6-9 can also utilize the cooling technique of FIG. 1 wherein block 12 and/or block 42 is utilized both to cool diode bars 11 and to cool the surface of the skin or other media 18. The embodiment of FIG. 7 is not as effective for achieving this objective as some of the other embodiments.

Figure 12:
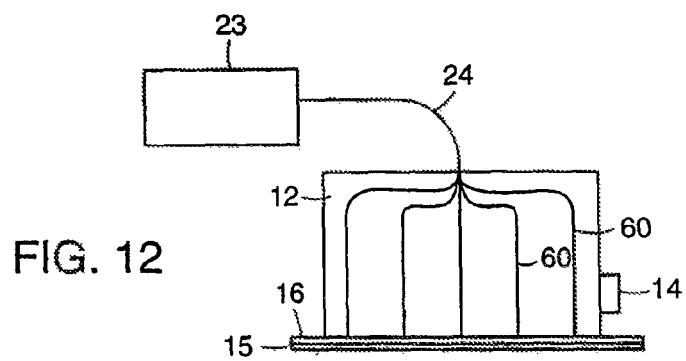
FIG. 12 is a cutaway, side elevation, semi-schematic representation of a fourth embodiment of the invention.

While for the embodiments described above, diode bars have been mounted in block 12 of head 10, in some applications other light emitters, for example filament lamps such as halogen lamps, could be suitably mounted in block 12 in place of the diode bars. Many of the advantages of this invention could also be achieved if a light pipe receiving light from a laser or other light emitting source is substituted for each diode bar 11 for the various embodiments. For example, FIG. 12 shows a head 10' which differs from that shown in FIG. 1 in that light from a laser or other light energy emitter of suitable power and wavelength is passed through a light pipe in lines 24 to a network of light pipes 60 in block 12, there being a plurality of light pipes 60 behind each light pipe shown to provide substantially the same light emission pattern as for the plurality of emitters 11A of each diode bar 11. The minimum aperture size D to achieve a selected amplification (f) from retroreflection is also applicable to substantially any laser or other light energy emitting head used on a scattering medium, including those shown in various prior patents and applications including U.S. Pat. Nos. 5,595,568; 5,735,844; 5,824,023, and application Ser. No. 09/078,055, FIG. 4 of which, for example, shows a head which may be used in practicing the teachings of this invention, but which differs from FIG. 12 in that the light pipes are angled to focus the light energy. Where light pipes are utilized, transparent layer or element may not be required, and reflective coating 16 can be applied directly to the bottom surface of block 12, with openings in the coating being provided under each light pipe.

Further, transparent layer 15 is preferably spaced by at least several micron, for example 50-100 microns, from the diode bars to assure against shorting of the laser bars, and this space may be filled with air or other gas, or with a liquid or solid insulating material which is transparent at least in the areas under the openings or slits in the reflective layer 16. For this embodiment, the spacing may be such that cooling of the medium from block 12 is no longer possible.

An invention has thus been disclosed, including a number of embodiments and various species of each embodiment, which provides a simpler cooling mechanism for certain embodiments for the surface of a medium undergoing a laser or other optical energy procedure and which also provides more optimum, and in some cases substantially optimum, use of light energy produced by diode laser bars, or other optical energy source, even when the light is being delivered to a highly scattering medium, by designing the device to provide an adequate input aperture and suitable mechanisms for retroreflecting such light. Further, while a number of embodiments and species thereof have been disclosed, it is apparent that these are being provided for purposes of illustration only and that other similar or equivalent mechanisms might also be employed. Thus, while the invention has been particularly shown and described above with reference to preferred embodiments and species, the foregoing and other changes in form and detail may be made therein by one skilled in the art without departing from the spirit and scope of the invention, which is to be defined only by the appended claims.

What is claimed is:

1. A light energy treatment head comprising:
   a thermally conductive transparent element configured for contact with the skin;
   at least one diode laser mounted within the head and oriented to direct optical energy through the thermally conductive transparent element to a target region of skin during use; and
   at least one cooling mechanism for extracting heat from both the thermally conductive transparent element and the at least one diode laser.

2. The light energy treatment head of claim 1, wherein the at least one cooling mechanism comprises at least one coolant flow channel.

3. The light energy treatment head of claim 1, wherein the at least one cooling mechanism comprises a thermoelectric cooling element.

4. The light energy treatment head of claim 1, further comprising a reflective mask disposed between the at least one diode laser and the target skin region, wherein said mask has an opening formed therein through which optical energy may be applied to said target region.

5. The light energy treatment head of claim 4, wherein the reflective mask is a coating of reflective material.

6. The light energy treatment head of claim 4, wherein the reflective mask has an area at least substantially as large as an aperture of reflection for scattered optical energy from said target region.

7. The light energy treatment head of claim 1, wherein said transparent element is a waveguide.

8. The light energy treatment head of claim 7, wherein said waveguide further comprises an angle dependent reflecting layer on at least one wall of said waveguide capable of attenuating angled optical energy entering said waveguide.

9. The light energy treatment head of claim 1, wherein the at least one diode laser is mounted in a mount.

10. The light energy treatment head of claim 9, wherein the mount is thermally conductive.

11. The light energy treatment head of claim 9, wherein the mount is a heat sink for sinking heat from both the diode laser and the transparent element.

12. The light energy treatment head of claim 9, wherein the mount has at least one groove, wherein the at least one diode laser is mounted in said at least one groove.

13. The light energy treatment head of claim 9, further comprising a reflecting layer in proximity to the transparent element, wherein said reflecting layer has an opening formed therein under the at least one diode laser through which optical energy may be applied to said target region.

14. The light energy treatment head of claim 9, wherein the transparent element has a larger surface area than the surface area of said mount.

15. The light energy treatment head of claim 9, further comprising a reflecting layer in proximity to the transparent element, wherein the reflecting layer has a larger area than the area of said mount.

16. The light energy treatment head of claim 1, wherein the cooling mechanism is further capable of cooling the target region.

* * * * *